United States Patent [19]
Edwards et al.

[11] Patent Number: 5,843,021
[45] Date of Patent: Dec. 1, 1998

[54] CELL NECROSIS APPARATUS

[75] Inventors: Stuart D. Edwards, Portola Valley, Calif.; Ronald G. Lax, Palm City, Fla.

[73] Assignee: Somnus Medical Technologies, Inc., Sunnyvale, Calif.

[21] Appl. No.: 905,991

[22] Filed: Aug. 5, 1997

Related U.S. Application Data

[63] Continuation-in-part of Ser. No. 642,327, May 3, 1996, which is a continuation-in-part of Ser. No. 606,195, Feb. 23, 1996, Pat. No. 5,707,349, which is a continuation-in-part of Ser. No. 516,781, Aug. 18, 1995, Pat. No. 5,674,191, which is a continuation-in-part of Ser. No. 239,658, May 9, 1994, Pat. No. 5,456,662.

[51] Int. Cl.$^6$ .................................................. A61B 17/39
[52] U.S. Cl. ................................................................ 604/22
[58] Field of Search ................... 604/21, 22; 606/27–34, 606/37–42, 45–52, 110, 111; 607/96–102, 134, 135, 154, 156

[56] References Cited

U.S. PATENT DOCUMENTS

| | | | |
|---|---|---|---|
| 3,901,241 | 8/1975 | Allen | 128/303.1 |
| 4,011,872 | 3/1977 | Komiya | 128/303.14 |
| 4,411,266 | 10/1983 | Cosman | 128/303.18 |
| 4,423,812 | 1/1984 | Sato | 206/387 |
| 4,532,924 | 8/1985 | Auth et al. | 128/303.17 |
| 4,565,200 | 1/1986 | Cosman | 128/642 |
| 4,901,737 | 2/1990 | Toone | 128/848 |
| 4,906,203 | 3/1990 | Margrave et al. | 439/188 |
| 4,907,589 | 3/1990 | Cosman | 606/34 |

(List continued on next page.)

FOREIGN PATENT DOCUMENTS

| | | |
|---|---|---|
| WO 92/10142 | 6/1992 | WIPO . |
| WO 93/08755 | 5/1993 | WIPO . |
| WO 94/10925 | 5/1994 | WIPO . |
| WO 95/18575 | 7/1995 | WIPO . |
| Wo 96/29946 | 10/1996 | WIPO . |

OTHER PUBLICATIONS

Kaneko, et al., *Physiological Laryngeal Pacemaker*, May 1985, Trans Am Soc Artif Intern Organs, vol. XXXI, pp. 293–296.

Mugica, et al., *Direct Diaphragm Stimulation*, Jan., 1987, PACE, vol. 10, pp. 252–256.

Mugica, et al., Nuerostimulation: An Overview, Chapter 21, *Preliminary Test of a Muscular Diaphram Pacing System on Human Patients*, 1985, pp. 263–279.

Nochomovitz, et al., *Electrical Activiation of the Diaphragm*, Jun. 1988, Clinics in Chest Medicine, vol. 9, No. 2, pp. 349–358.

Prior, et al., *Treatment of Menorrhagia by Radiofrequency Heating*, 1991, INt. J. Hyperthermia, vol. 7, pp. 213–220.

Rice, et al., Endoscopic Paranasal Sinus Surgery, Chapter 5, *Funtional Endoscopic Paranassal Sinus Surgery, The Technique of Messeklinger*, Raven Press, 1988, pp. 75–104.

Rice, et al. Endoscopic Paranasal Sinus Surgery, Chapter 6, *Total Endoscopic Sphenoethmoidectomy, The Technique of Wigand*, Raven Press, 1988, pp. 105–125.

*Primary Examiner*—Manuel Mendez
*Attorney, Agent, or Firm*—Wilson Sonsini Goodrich & Rosati

[57] ABSTRACT

An apparatus that reduces a volume of a selected site in an interior of the tongue includes a handpiece means and an electrode means at least partially positioned in the interior of the handpiece means. The electrode means includes an electrode means electromagnetic energy delivery surface and is advance able from the interior of the handpiece means into the interior of the tongue. An electrode means advancement member is coupled to the electrode means and configured to advance the electrode means an advancement distance in the interior of the tongue. The advancement distance is sufficient for the electrode means electromagnetic energy delivery surface to deliver electromagnetic energy to the selected tissue site and reduce a volume of the selected site without damaging a hypoglossal nerve. A cable means is coupled to the electrode means.

83 Claims, 15 Drawing Sheets

U.S. PATENT DOCUMENTS

| | | | |
|---|---|---|---|
| 4,947,842 | 8/1990 | Marchosky et al. | 128/401 |
| 4,966,597 | 10/1990 | Cosman | 606/50 |
| 4,976,711 | 12/1990 | Parins et al. | 606/48 |
| 5,046,512 | 9/1991 | Murchie | 128/848 |
| 5,057,107 | 10/1991 | Parins et al. | 606/48 |
| 5,078,717 | 1/1992 | Parins et al. | 606/48 |
| 5,083,565 | 1/1992 | Parins | 128/642 |
| 5,094,233 | 3/1992 | Brennan | 602/6 |
| 5,100,423 | 3/1992 | Fearnot | 606/159 |
| 5,122,137 | 6/1992 | Lennox | 606/40 |
| 5,125,928 | 6/1992 | Parins et al. | 606/48 |
| 5,190,541 | 3/1993 | Abele et al. | 606/46 |
| 5,197,963 | 3/1993 | Parins | 606/46 |
| 5,197,964 | 3/1993 | Parins | 606/48 |
| 5,215,103 | 6/1993 | Desai | 128/784 |
| 5,257,451 | 11/1993 | Edwards et al. | 29/825 |
| 5,275,162 | 1/1994 | Edwards et al. | 128/642 |
| 5,277,201 | 1/1994 | Stern | 607/98 |
| 5,281,217 | 1/1994 | Edwards et al. | 606/41 |
| 5,281,218 | 1/1994 | Imran | 606/41 |
| 5,290,286 | 3/1994 | Parins | 606/50 |
| 5,293,869 | 3/1994 | Edwards et al. | 128/642 |
| 5,309,910 | 5/1994 | Edwards et al. | 128/642 |
| 5,313,943 | 5/1994 | Houser et al. | 128/642 |
| 5,314,466 | 5/1994 | Stern et al. | 607/156 |
| 5,328,467 | 7/1994 | Edwards et al. | 604/95 |
| 5,348,554 | 9/1994 | Imran et al. | 606/41 |
| 5,363,861 | 11/1994 | Edwards et al. | 128/772 |
| 5,365,926 | 11/1994 | Desai | 128/642 |
| 5,366,490 | 11/1994 | Edwards et al. | 607/99 |
| 5,368,592 | 11/1994 | Stern et all. | 606/33 |
| 5,370,675 | 12/1994 | Edwards et al. | 607/101 |
| 5,370,678 | 12/1994 | Edwards et al. | 607/101 |
| 5,383,876 | 1/1995 | Nardella | 606/49 |
| 5,383,917 | 1/1995 | Desai | 607/702 |
| 5,385,544 | 1/1995 | Edwards et al. | 604/22 |
| 5,397,339 | 3/1995 | Desai | 687/116 |
| 5,398,683 | 3/1995 | Edwards et al. | 128/642 |
| 5,403,311 | 4/1995 | Abele et al. | 606/49 |
| 5,409,453 | 4/1995 | Kundquist et al. | 604/22 |
| 5,421,819 | 6/1995 | Edwards et al. | 604/22 |
| 5,423,808 | 6/1995 | Edwards et al. | 606/34 |
| 5,423,811 | 6/1995 | Imran et al. | 606/41 |
| 5,433,739 | 7/1995 | Sluijter et al. | 607/99 |
| 5,435,805 | 7/1995 | Edwards et al. | 604/22 |
| 5,456,662 | 10/1995 | Edwards et al. | 604/22 |
| 5,456,682 | 10/1995 | Edwards et al. | 606/31 |
| 5,458,596 | 10/1995 | Lax et al. | 606/31 |
| 5,458,597 | 10/1995 | Edwards et al. | 606/41 |
| 5,470,308 | 11/1995 | Edwards et al. | 604/22 |
| 5,471,982 | 12/1995 | Edwards et al. | 128/642 |
| 5,472,441 | 12/1995 | Edwards et al. | 606/41 |
| 5,484,400 | 1/1996 | Edwards et al. | 604/22 |
| 5,486,161 | 1/1996 | Lax et all. | 604/22 |
| 5,505,730 | 4/1996 | Edwards | 606/41 |
| 5,507,743 | 4/1996 | Edwards et al. | 606/41 |
| 5,509,419 | 4/1996 | Edwards et al. | 128/642 |
| 5,514,130 | 5/1996 | Baker | 606/41 |
| 5,514,131 | 5/1996 | Edwards et al. | 606/45 |
| 5,520,684 | 5/1996 | Imran | 606/41 |
| 5,531,676 | 7/1996 | Edwards et al. | 604/22 |
| 5,531,677 | 7/1996 | Lundquist et al. | 604/22 |
| 5,536,240 | 7/1996 | Edwards et al. | 604/22 |
| 5,536,267 | 7/1996 | Edwards et al. | 606/41 |
| 5,540,655 | 7/1996 | Edwards et al. | 604/22 |
| 5,542,915 | 8/1996 | Edwards et al. | 604/22 |
| 5,542,916 | 8/1996 | Hirsch et al. | 604/22 |
| 5,545,161 | 8/1996 | Imran | 606/41 |
| 5,545,171 | 8/1996 | Sharkey et al. | 606/148 |
| 5,545,193 | 8/1996 | Fleischman et al. | 607/99 |
| 5,549,108 | 8/1996 | Edwards et al. | 128/642 |
| 5,549,644 | 8/1996 | Lundquist et al. | 604/22 |
| 5,554,110 | 9/1996 | Edwards et al. | 604/22 |
| 5,556,377 | 9/1996 | Rosen et al. | 604/22 |
| 5,558,672 | 9/1996 | Edwards et al. | 606/41 |
| 5,558,673 | 9/1996 | Edwards et al. | 606/41 |

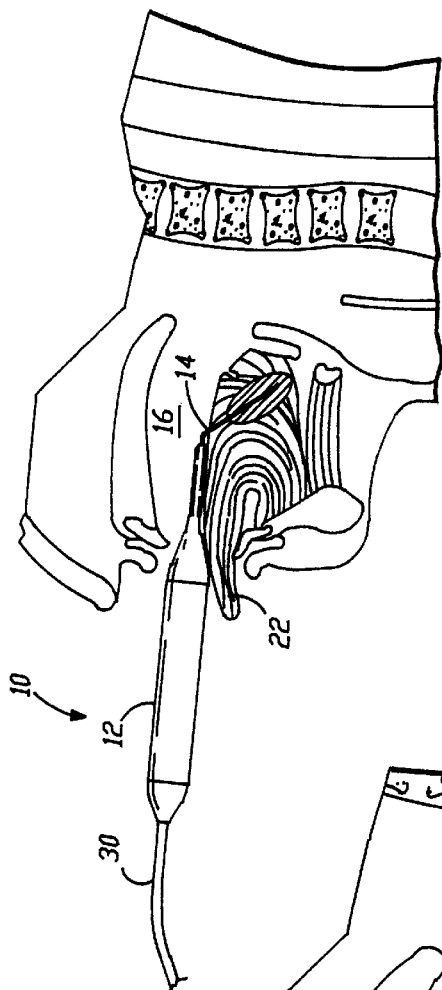
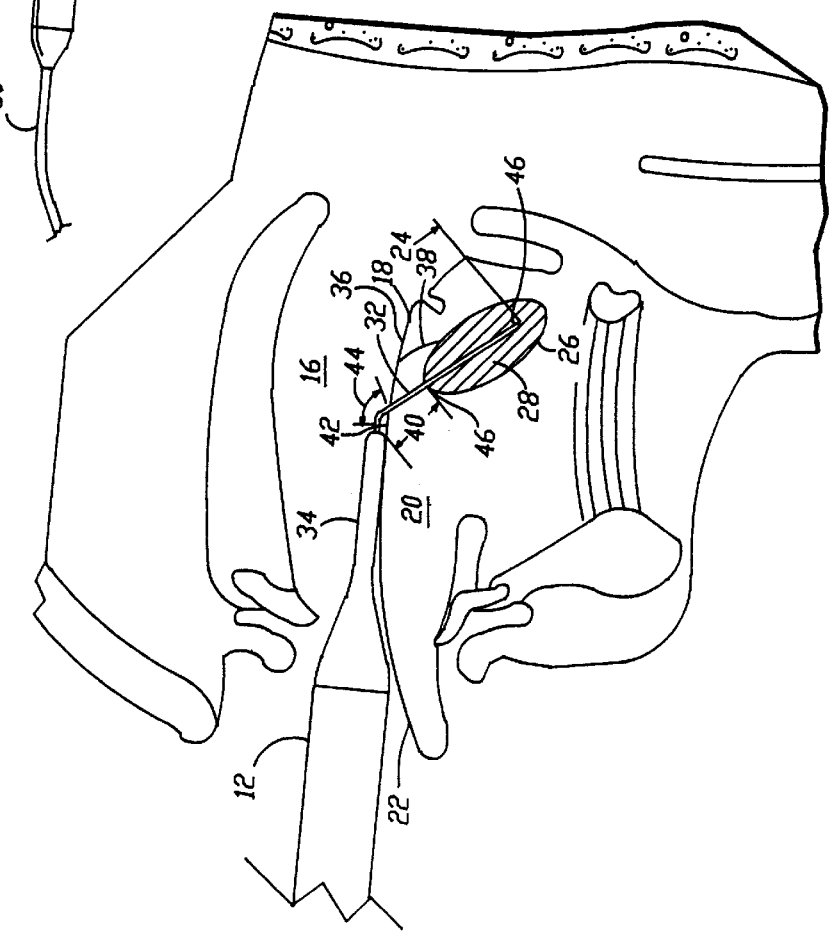
FIG. – 1A
FIG. – 1B

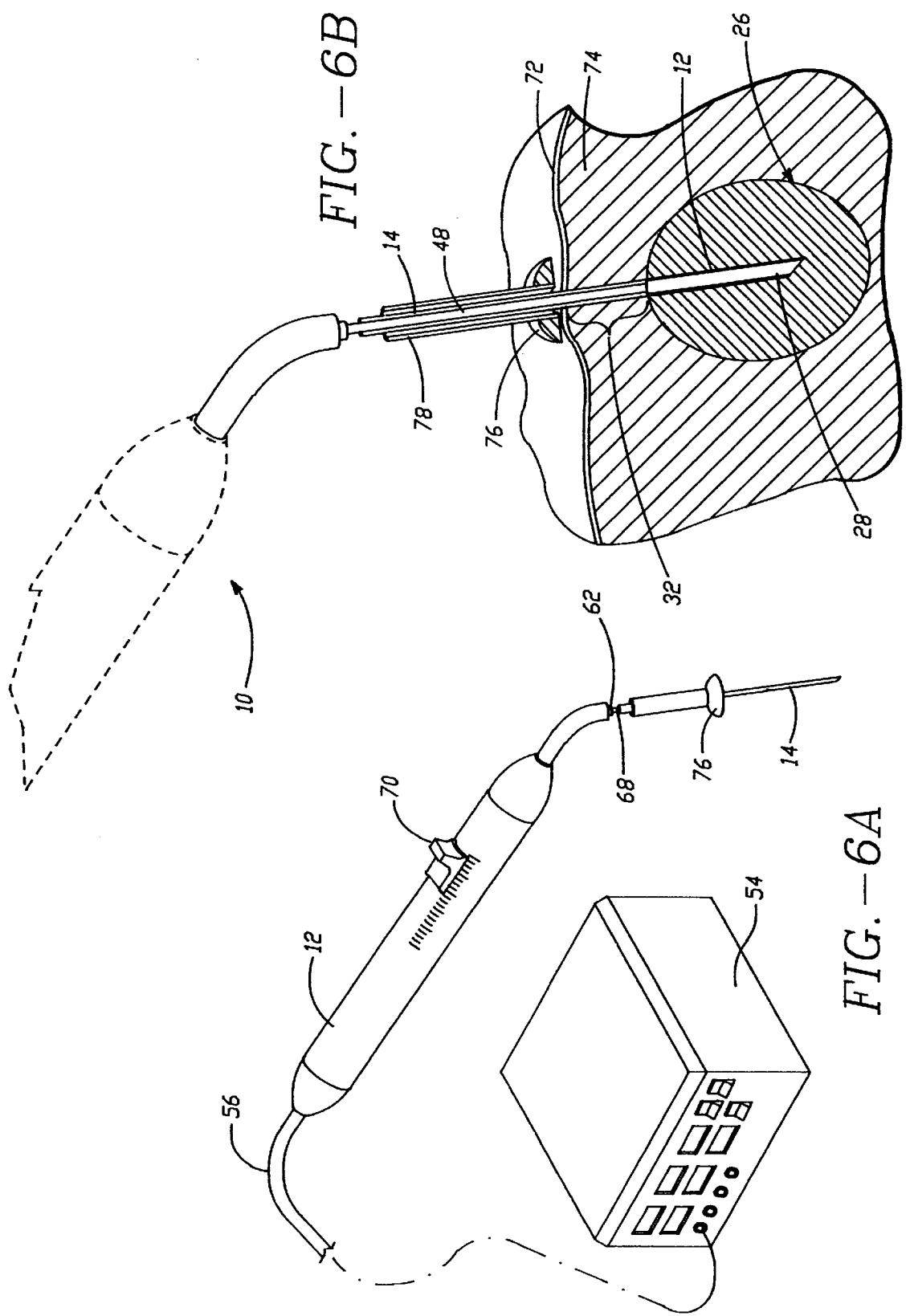

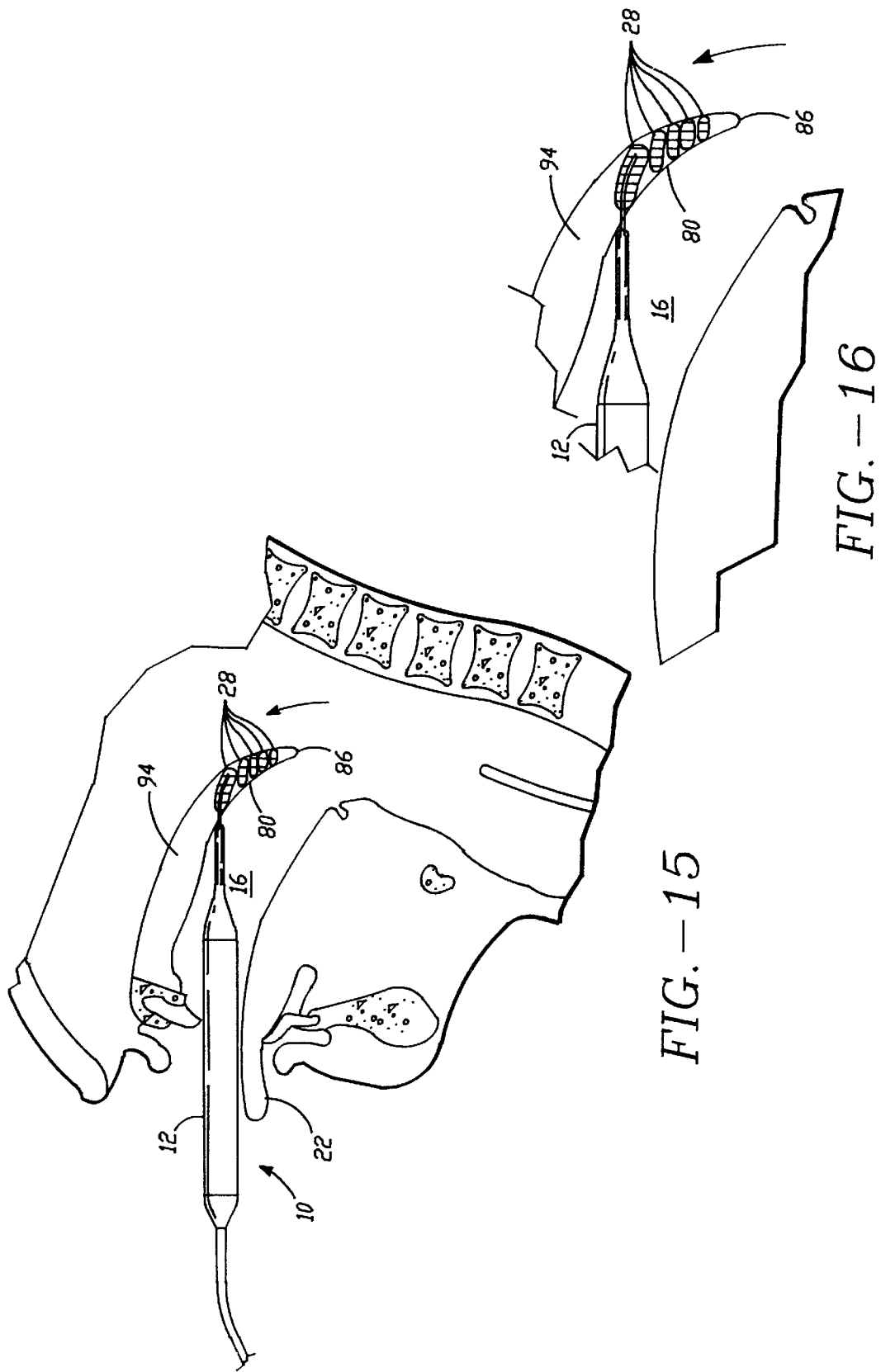

CELL NECROSIS APPARATUS

CROSS-REFERENCE TO RELATED APPLICATIONS

This application is a continuation-in-part of allowed U.S. patent application Ser. No. 08/642,327, filed May 3, 1996, entitled "Method for Treatment of Airway Obstructions", which application is a continuation-in-part application of U.S. patent application Ser. No. 08/606,195, filed Feb. 23, 1996, entitled "Method for Treatment of Airway Obstructions", now U.S. Pat. No. 5,707,349 which is a continuation in part of U.S. patent application Ser. No. 08/516,781 filed Aug. 18, 1995, entitled "Ablation Apparatus and System for Removal of Soft Palate Tissue", now U.S. Pat. No. 5,674,191, having named inventors Stuart D. Edwards, Edward J. Gough and David L. Douglass, which is a continuation-in-part of U.S. application Ser. No. 08/239,658, filed May 9, 1994 entitled "Method for Reducing Snoring by RF Ablation of the Uvula", now U.S. Pat. No. 5,456,662, all incorporated by reference herein.

BACKGROUND OF THE INVENTION

1. Field of the Invention

This invention relates to an apparatus for the treatment of air way obstructions, and more particularly to an apparatus for creating selective cell necrosis in interior sections of selected head and neck structures without damaging vital structures.

2. Description of Related Art

Sleep-apnea syndrome is a medical condition characterized by daytime hypersomnomulence, morning arm aches, intellectual deterioration, cardiac arrhythmias, snoring and thrashing during sleep. It is caused by frequent episodes of apnea during the patient's sleep. The syndrome is classically subdivided into two types. One type, termed "central sleep apnea syndrome", is characterized by repeated loss of respiratory effort. The second type, termed obstructive sleep apnea syndrome, is characterized by repeated apneic episodes during sleep resulting from obstruction of the patient's upper airway or that portion of the patient's respiratory tract which is cephalad to, and does not include, the larynx.

Treatment thus far includes various medical, surgical and physical measures. Medical measures include the use of medications such as protriptyline, medroxyprogesterone, acetazolamide, theophylline, nicotine and other medications in addition to avoidance of central nervous system depressants such as sedatives or alcohol. The medical measures above are sometimes helpful but are rarely completely effective. Further, the medications frequently have undesirable side effects.

Surgical interventions have included uvulopalatopharyngoplasty, tonsillectomy, surgery to correct severe retrognathia and tracheostomy. In one type of surgical intervention a standard LeFort I osteotomy is combined with a sagittal split ramus osteotomy to advance the maxilla, mandible and chin. Such a procedure may be effective but the risk of surgery in these patients can be prohibitive and the procedures are often unacceptable to the patients.

Physical measures have included weight loss, nasopharyngeal airways, nasal CPAP and various tongue retaining devices used nocturnally. These measures may be partially effective but are cumbersome, uncomfortable and patients often will not continue to use these for prolonged periods of time. Weight loss may be effective but is rarely achieved by these patients.

In patients with central sleep apnea syndrome, phrenic nerve or diaphragmatic pacing has been used. Phrenic nerve or diaphragmatic pacing includes the use of electrical stimulation to regulate and control the patient's diaphragm which is innervated bilaterally by the phrenic nerves to assist or support ventilation. This pacing is disclosed in *Direct Diaphragm Stimulation* by J. Mugica et al. PACE vol. 10 Jan–Feb. 1987, Part II, *Preliminary Test of a Muscular Diaphragm Pacing System on Human Patients* by J. Mugica et al. from Neurostimulation: An Overview 1985 pp. 263–279 and *Electrical Activation of Respiration* by Nochomovitez IEEE Eng. in Medicine and Biology; June, 1993.

However, it was found that many of these patients also have some degree of obstructive sleep apnea which worsens when the inspiratory force is augmented by the pacer. The ventilation induced by the activation of the diaphragm also collapses the upper airway upon inspiration and draws the patient's tongue inferiorly down the throat choking the patient. These patients then require tracheostomies for adequate treatment.

A physiological laryngeal pacemaker as described in *Physiological Laryngeal Pacemaker* by F. Kaneko et al. from Trans Am Soc Artif Intern Organs 1985 senses volume displaced by the lungs and stimulates the appropriate nerve to open the patient's glottis to treat dyspnea. This apparatus is not effective for treatment of sleep apnea. The apparatus produces a signal proportional in the displaced air volume of the lungs and thereby the signal produced is too late to be used as an indicator for the treatment of sleep apnea. There is often no displaced air volume in sleep apnea due to obstruction.

One measure that is effective in obstructive sleep apnea is tracheostomy. However, this surgical intervention carries considerable morbidity and is aesthetically unacceptable to many patients. Other surgical procedures include a standard Le Fort I osteotomy in combination with a sagittal split ramus osteotomy. This is a major surgical intervention that requires the advancement of the maxilla, mandible and chin.

Generally, there are two types of snoring. They are distinguished, depending on the localization of their origin. The first type of snoring, velar, is produced by the vibration of all of the structures of the soft palate including the velum, the interior and posterior arches of the tonsils and the uvula. Velar snoring results from a vibration of the soft palate created by the inspiratory flow of air, both nasal and oral, which makes the soft palate wave like a flag. The sound intensity of these vibrations is accentuated by the opening of the buccal cavity which acts as a sound box.

The second type, pharyngeal snoring, is a kind of rattle, including even horn whistling. It is caused by the partial obstruction of the oropharyngeal isthmus by the base of the tongue with, now and again, its total exclusion by the tongue base becoming jammed against the posterior wall of the pharynx. This results in a sensation of breathing, apnea, which constitutes the sleep apnea syndrome. These two types of snoring may easily be combined in the same individual.

For some years there have been surgical techniques for correcting apnea. However, maxillary surgery to cure pharyngeal snoring requires major surgery, with the operation lasting several hours, and the uvula-palatopharnygoplasty procedure to correct velar snoring is not without draw backs. This explains the popularity of prosthesis and other preventive devices.

More recently, portions of the soft palate have been removed by laser ablation. If too much tissue is removed, severe consequences result. The degree of laser ablation is difficult to control and multiple treatments are usually required. Further, patients have a high degree of soreness in their throats for many weeks.

U.S. Pat. No. 4,423,812 discloses a loop electrode design characterized by a bare active wire portion suspended between wire supports on an electrode shaft. Tissue striping is effected with a bare wire, and the adjacent portions of the wire supports an electrode shaft that is made insulating to prevent accidental burns to the patient, allowing the physician to use these insulated parts to help position and guide the active wire portion during the surgical procedure. However, this requires that the physician shave off, during multiple visits, successive thin superficial layers of the obstructing tissues to avoid gross resection and its adverse affects.

U.S. Pat. No. 5,046,512 discloses a method for the treatment of snoring and apnea. The method regulates air flow to the user to an extent comparable to the volume of air which flows through the users nasal passages. An associated apparatus provides a device having a body portion sufficiently wide to separate the users teeth. It includes an air passage comparable in area to the area of the user's nasal passages.

The use of oral cavity appliances has been proposed frequently for the treatment of sleep disorders. It has been recognized that movement of the mandible forward relative to the maxilla can eliminate or reduce sleep apnea and snoring symptoms by causing the pharyngeal air passage to remain open. Several intra-oral dental appliances have been developed which the user wears at night to fix the mandible in an anterior protruded position. Such dental appliances essentially consist of acrylic or elastomeric bit blocks, similar to orthodontic retainers or athletic mouth guards, which are custom fitted to a user's upper and lower teeth. The device may be adjusted to vary the degree of anterior protrusion.

U.S. Pat. No. 4,901,737 discloses an intra-oral appliance while reducing snoring which repositions the mandible in an inferior, open, and anterior, protrusive, position as compared to the normally closed position of the jaw. Once the dentist or physician determines the operative snoring reduction position for a particular patient, an appropriate mold is taken for the maxillary dentition and of the mandibular dentition to form an appliance template. This device includes a pair of V-shaped spacer members formed from dental acrylic which extend between the maxillary and mandibular dentition to form a unitary mouthpiece.

While such dental appliances have proven effective in maintaining the mandible in a protruded position to improve airway patency, they often result in undesirable side effects. One of the most common side effects is aggravation of the tempromandibular joint and related jaw muscles and ligaments, especially in individuals who have a tendency to grind their teeth during sleep. Aggravation of the tempromandibular joint has be associated with a wide variety of physical ailments, including migraine headaches. Accordingly, many individuals suffering from sleep apnea and snoring disorders are not able to tolerate existing anti-snoring dental appliances for long periods of time.

Opening of obstructed nasal airways by reducing the size of the turbinates has been performed using surgical and pharmaceutical treatments. Examples of surgical procedures include anterior and posterior ethmoidectomy, such as those described in "Endoscopic Paranasal Sinus Surgery" by D. Rice and S. Schaefer, Raven Press, 1988); the writings of M. E. Wigand, Messerklinger and Stamberger; and U.S. Pat. No. 5,094,233. For example, as described in U.S. Pat. No. 5,094,233, the Wigand procedure involves the transection of the middle turbinate, beginning with the posterior aspect, visualization of the sphenoid ostium and opening of the posterior ethmoid cells for subsequent surgery. In the sphenoidectomy step, the ostium of the sphenoid is identified and the anterior wall of the sinus removed. Following this step, the posterior ethmoid cells may be entered at their junction with the sphenoid and the fovea ethmoidalis can be identified as an anatomical landmark for further dissection. In anterior ethmoidectomy, the exenteration of the ethmoids is carried anteriorly to the frontal recess. Complications, such as hemorrhage, infection, perforation of the fovea ethmoidalis or lamina papyracea, and scarring or adhesion of the middle turbinate, are reported in connection with these procedures.

One of the problems encountered as a result of these procedures is postoperative adhesion occurring between the turbinates and adjacent nasal areas, such as medial adhesion to the septum and lateral adhesion to the lateral nasal wall in the area of the ethmoid sinuses. Otherwise successful surgical procedures may have poor results in these cases. Some surgeons have proposed amputation of a portion of the turbinate at the conclusion of surgery to avoid this complication, resulting in protracted morbidity (crust formation and nasal hygiene problems). The turbinate adhesion problem detracts from these endoscopic surgical procedures. Efforts have been made to reduce the complications associated with the surgical treatment of turbinate tissue, for example by the use of a turbinate sheath device. U.S. Pat. No. 5,094,233.

U.S. Pat. No. 3,901,241 teaches a cryosurgical instrument which is said to be useful for shrinking nasal turbinates. U.S. Pat. No. 3,901,241.

Pharmaceuticals have also been developed for reducing the size of the turbinates. However, pharmaceuticals are not always completely efficacious and generally do not provide a permanent reduction in turbinate size. In addition, pharmaceuticals can have adverse side effects.

A need exists for a method and device for clearing obstructed nasal passageways. It is preferred that the method and device be performable with minimal surgical intervention or post operative complications. It is also preferred that the method and device reduce the size of the turbinate structure without involving surgical cutting or the physical removal of tissue. It is also preferred that the method and device provide a reduction in turbinate structure size to increase air flow in the nasal passageway sufficiently impairing blood flow to the optic nerve and/or retina and create a permanent impairment of vision by the ablation.

It would be desirable to provide an ablation apparatus which eliminates the need for dental appliances for the treatment of snoring and sleep apnea disorders. It would also be desirable to provide a treatment device which is not an intra-oral dental appliance, and which can effectively and safely remove selected portions of the soft palate without providing the patient with undesirable side effects. Further, it would be desirable to provide a tissue ablation device which retains the targeted ablation tissue during the ablation process.

It would be desirable to provide an apparatus for the treatment of snoring which reduces the size of the soft palate and/or uvula with a minimal amount of cutting. It would also be desirable to provide an apparatus for the treatment snoring which is configured to position at least a portion of an energy delivery device into an interior of the soft palate and/or uvula to deliver ablation energy to the interior in order to reduce the size of the soft palate and/or uvula.

SUMMARY OF THE INVENTION

Accordingly, an object of the invention is to provide an apparatus for selective cell necrosis at selected site of different head and neck structures.

Another object of the invention is to provide an apparatus to treat airway obstructions.

Yet another object of the invention is to provide an apparatus that provides controlled cell necrosis of the tongue.

A further object of the invention is to provide an apparatus that provides controlled cell necrosis of the uvula and other soft palate structures.

Still another object of the invention is to provide an apparatus that provides controlled cell necrosis of turbinate structures.

These and other objects of the invention are achieved in a cell necrosis apparatus to reduce a volume of a selected site in an interior of a tongue in an oral cavity. The apparatus includes a handpiece means. An electrode means is coupled to a distal portion of the handpiece means and includes a tissue piercing distal end. The electrode means is configured to be maneuverable in the oral cavity to pierce a tongue surface and advance into an interior of the tongue a sufficient distance to a tissue site, deliver electromagnetic energy to the tissue site and create cell necrosis without damaging a main branch of the hypoglossal nerve. A cable means is coupled to the electrode means.

In another embodiment of the invention, a cell necrosis apparatus reduces a volume of a selected site in an interior of a uvula. The apparatus includes a handpiece means. An electrode means is coupled to a distal portion of the handpiece means and includes a tissue piercing distal end. The electrode means is configured to be maneuverable in the oral cavity to pierce a uvula surface, advance into an interior of the uvula a sufficient distance to a tissue site, deliver electromagnetic energy to the tissue site, create controlled cell necrosis and reposition the uvula in an oral cavity with reduced necrosis of an exterior mucosal surface of the uvula. A cable means is coupled to the electrode means.

In another embodiment of the invention, a cell necrosis apparatus to reduce a volume of a selected site in an interior of a turbinate structure. The apparatus includes a handpiece means. An electrode means is coupled to a distal portion of the handpiece means including a tissue piercing distal end. The electrode means is configured to be maneuverable in a nostril to pierce a turbinate structure surface, advance into an interior of the turbinate structure a sufficient distance to a tissue site, deliver electromagnetic energy to the tissue site, create controlled cell necrosis of the turbinate structure to increase a size of a nasal passageway. The cell necrosis apparatus delivers insufficient electromagnetic energy to impair blood flow to the optic nerve and/or retina and create a permanent impairment of vision. A cable means is coupled to the electrode means.

In another embodiment of the invention, a cell necrosis apparatus reduces a volume of a selected site in an interior of a soft palate structure. The apparatus includes a handpiece means. An electrode means is coupled to a distal portion of the handpiece means including a tissue piercing distal end. The electrode means is configured to be maneuverable in an oral cavity to pierce a soft palate structure surface, advance into an interior of the soft palate structure a sufficient distance to a tissue site, deliver electromagnetic energy to the tissue site, create controlled cell necrosis and reposition the soft palate structure in an oral cavity with reduced necrosis of an exterior mucosal surface of the soft palate structure. A cable means is coupled to the electrode means.

BRIEF DESCRIPTION OF THE FIGURES

FIGS. 1A–B illustrate lateral view of the oral cavity and the positioning of the cell necrosis apparatus of the present invention in the oral cavity.

FIG. 6A illustrates a perspective view of the cell necrosis apparatus of the present invention coupled to an energy source.

FIG. 6B illustrates a close up cross-sectional view of a hollow electrode of the invention utilized to create a cell necrosis zone below a tissue surface.

FIG. 15 depicts a cross-sectional view of the head illustrating the creation of cell necrosis zones in the soft palate structure.

FIG. 16 depicts a cross-sectional view of the soft palate structure of FIG. 15 illustrating the repositioning of the soft palate structure following creation of the cell necrosis zones.

DETAILED DESCRIPTION

Figure 1C:
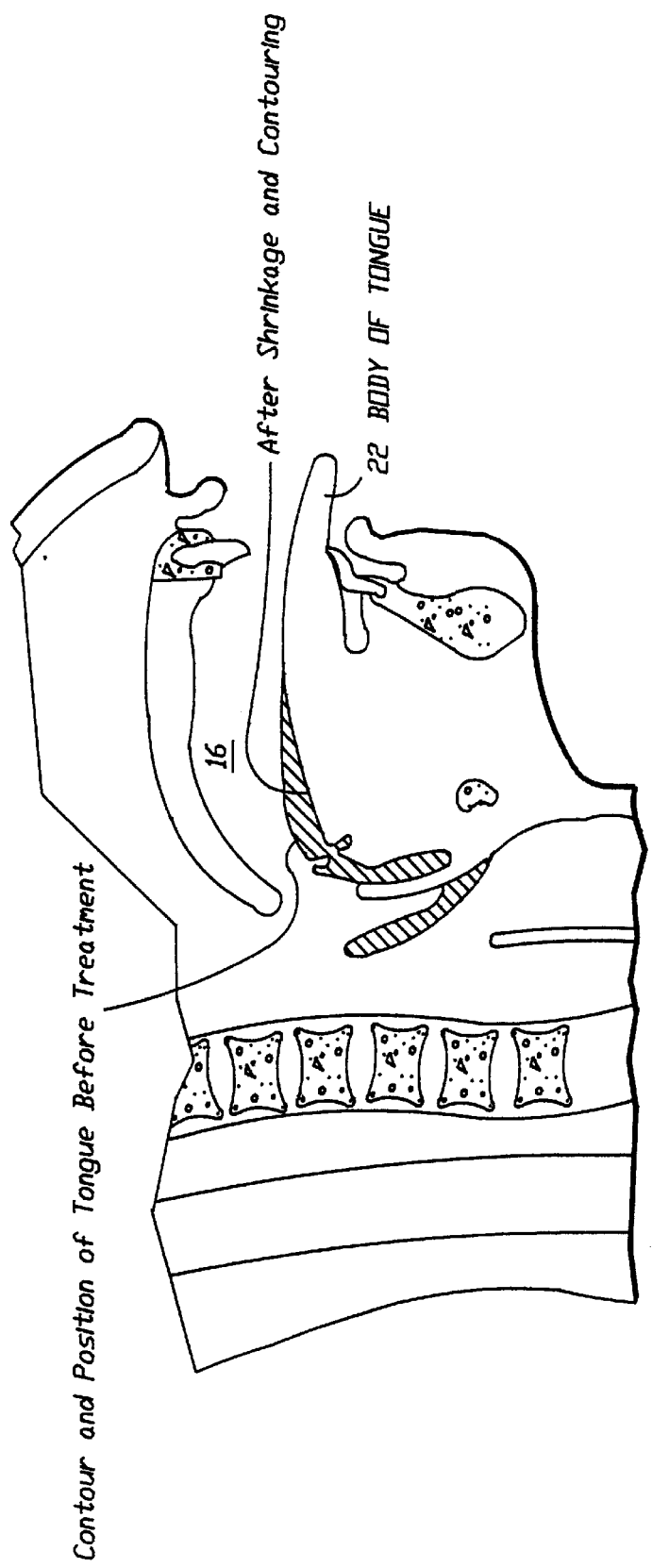
FIG. 1C depicts a lateral view of the oral cavity illustrating the repositioning of the tongue following treatment.

Referring now to FIGS. 1A–C, a cell necrosis apparatus 10 is used to reduce a volume of a selected site in an interior of a head and neck structure, and more particularly to a structure that is associated with an airway passage. Suitable anatomical structures include but are not limited to the tongue, uvula, soft palate tissue, tonsils, adenoids, turbinate structures and the like. In FIGS. 1A–C, cell necrosis apparatus 10 is shown as including a handpiece 12 coupled to an electrode 14. Handpiece 12 can be a proximal portion of electrode 14 that is suitable configured to enable placement and removal of cell necrosis apparatus to and from a selected anatomical structure and may include, in one embodiment, a proximal portion of electrode 12 that is insulated. Handpiece 12 and electrode 14 are sized and of a suitable geometry to be maneuverable in an oral cavity 16, pierce a tongue surface 18 and advance into an interior 20 of a tongue 22 a sufficient distance 24 to a tissue site 26. Electromagnetic energy is delivered to tissue site 26 to create cell necrosis at zone 28 without damaging a main branch of the hypoglossal nerve. A cable 30 is coupled to the electrode 14. For purposes of this disclosure, the main branches of the hypoglossal nerve are those branches which if damaged create an impairment, either partial or fill, of speech or swallowing capabilities. As shown in FIG. 1C, the treated structure of tongue 22 is repositioned in oral cavity 16. With this cell necrosis, the back of the tongue 22 moves in a forward direction (as indicated by the arrow) away from the air passageway. The result is an increase in the cross-sectional diameter of the air passageway.

Handle 14 is preferably made of an electrical and thermal insulating material. Electrode 14 can be made of a conductive material such as stainless steel. Additionally, electrode 14 can be made of a shaped memory metal, such as nickel titanium, commercially available from Raychem Corporation, Menlo Park, Calif. In one embodiment, only a distal end of electrode 14 is made of the shaped memory metal in order to effect a desired deflection.

Cell necrosis apparatus 10 can include visualization capability including but not limited to a viewing scope, an expanded eyepiece, fiber optics, video imaging, and the like.

Electrode 14 can include an insulator 32 which can be adjustable in length and in a surrounding relationship to an exterior surface of electrode 14. Insulator 32 serves as a barrier to thermal or RF energy flow. Insulator 32 can be in the form of an sleeve that may be adjustably positioned at the exterior of electrode 14. In one embodiment insulator can be made of a polyamide material and be a 0.002 inch shrink wrap. The polyamide insulating layer is semi-rigid.

Handpiece 12 can have a reduced diameter at a distal portion 34 to facilitate positioning, maneuverability, provide easier access to smaller openings and improve the visibility in the area where electrode 14 is to penetrate.

To use cell necrosis apparatus 10 in oral cavity 16, a topical and then a local anesthetic is applied to tongue 22. After a suitable period for the anesthesia to take effect, the physician may grasp the body of tongue 22 near the apex, using a gauze pad for a better grip. Tongue 22 is then drawn forward, bringing the body and the root of tongue 22 further forward for improved accessibility. Grasping handpiece 12, the physician positions a distal portion of electrode 14 at tongue surface 18. The position of electrode 14 in FIGS. 1A–C illustrates cell necrosis zone 28 below a mucosal surface 36 providing a protected zone 38. An insulated portion 40 of electrode 14 prevents delivery of energy to a main branch of a hypoglossal nerve and/or to mucosal surface 36.

Electrode 14 can have an angle 42 at a bend zone 44 which is lateral to a longitudinal axis of handpiece 12. Electrode 14 can be malleable to create different bend zones, depending on the anatomical structure and the insertion position of the anatomical structure. With the use of a bending fixture, not shown, the arc of angle 42 can be adjusted by the physician as needed at the time of treatment.

It will be appreciated that although the term "electrode" in the specification generally means an energy delivery device including but not limited to resistive heating, RF, microwave, ultrasound and liquid thermal jet. The preferred energy source is an RF source and electrode 14 is an RF electrode operated in either bipolar or monopolar mode with a ground pad electrode. In a monopolar mode of delivering RF energy, a single electrode 14 is used in combination with an indifferent electrode patch that is applied to the body to form the other contact and complete an electrical circuit. Bipolar operation is possible when two or more electrodes 14 are used. Multiple electrode 14 may be used.

When the energy source is RF, an RF energy source may have multiple channels, delivering separately modulated power to each electrode 14. This reduces preferential heating that occurs when more energy is delivered to a zone of greater conductivity and less heating occurs around electrodes 14 which are placed into less conductive tissue. If the tissue hydration or blood infusion in the tissue is uniform, a single channel RF energy source may be used to provide power for the treatment and cell necrosis zones are relatively uniform in size.

One or more sensors 46 can be included and positioned at a distal end of electrode 14, at a distal end of insulator 32, as well as at other positions of cell necrosis apparatus 10. Sensor 46 is of conventional design, including but not limited to thermistors, thermocouples, resistive wires, and the like. A suitable sensor 46 is a T type thermocouple with copper constantene, J type, E type, K type, fiber optics, resistive wires, thermocouple IR detectors, and the like.

Electrode 14 can experience a steep temperature gradient as current moves outward the electrode 14. This causes the tissue that is immediately adjacent to electrode 14 to reach temperatures of 100 degrees C. or more while tissue only 5 to 10 mm away may be at or near body temperature. Because of this temperature gradient it is often necessary to place electrode 14 several times or use a plurality of electrodes 14 to create a cell necrosis zone 28 of the desired volume. Because of the aggressive heating immediately proximal of electrode 14 desiccation of tissue adjacent to electrode 14 may result. When the fluid within the tissue is desiccated, no electrical current flows through the tissue and the heating is then terminated. This problem can be solved by using a lower rate of heating which requires extended treatment periods.

Figure 3:
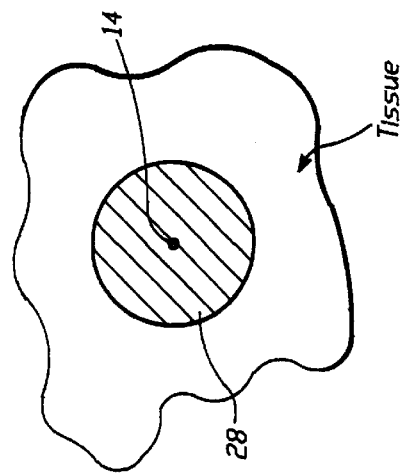
FIGS. 2–4 illustrate the creation of various cell necrosis zones.
Figure 2:
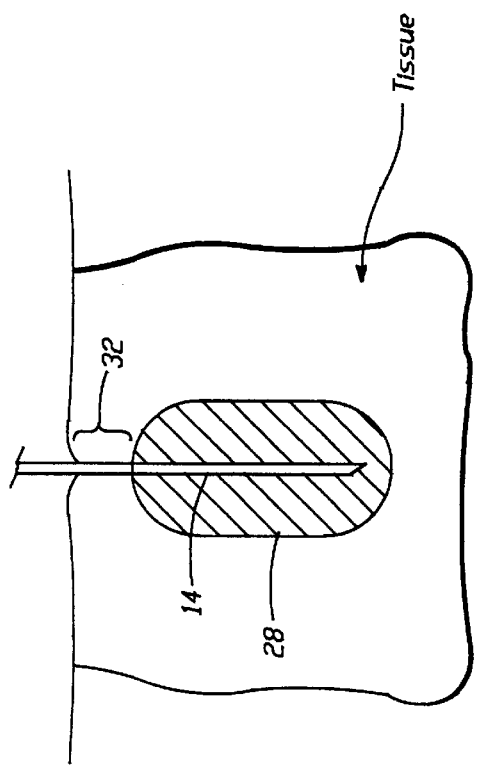
Figure 4:
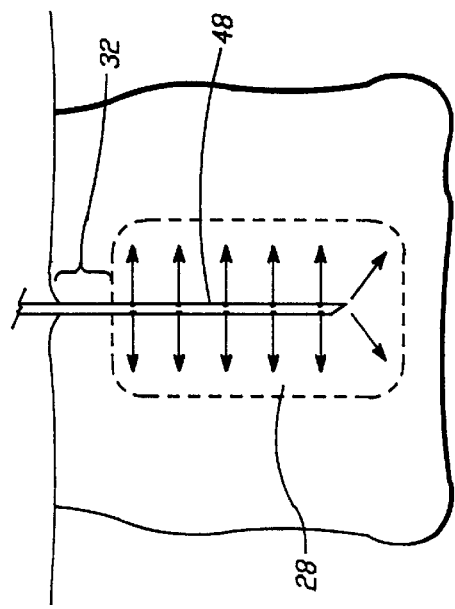

Referring now to FIGS. 2 through 4, an embodiment of the invention is disclosed where electrode 14 includes a hollow lumen 48 and a plurality of apertures through which a fluid medium can flow. Suitable fluid mediums include but are not limited to cooling and heating fluids, electrolytic solutions, chemical ablation medium, a disinfectant medium and the like.

A suitable electrolytic solution is saline, solutions of calcium salts, potassium salts, and the like. Electrolytic solutions enhance the electrical conductivity of the tissue. When a highly conductive fluid is infused into tissue, the ohmic resistance is reduced and the electrical conductivity of the infused tissue is increased. With this condition there will be little tendency for tissue surrounding electrode 14 to desiccate and the result is a large increase in the capacity of the tissue to carry RF energy. A zone of tissue which has been heavily infused with a concentrated electrolytic solution can then become so conductive as to actually act as an electrode. The effect of the larger (fluid) electrode is that greater amounts of current can be conducted, making it possible to heat a much greater volume of tissue in a given time period.

Figure 5:
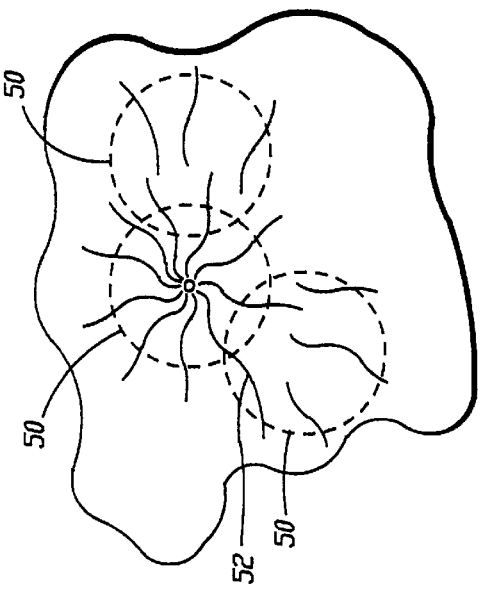
FIG. 5 illustrates the introduction of boluses solution to tissue.

In addition to the larger electrode area that results from infusion of an electrolytic solution it is then possible to inject one or more boluses 50 of electrolytic solution as shown in FIG. 5. RF current 52 can then flow through the infused tissue surrounding electrode 14 and follow the course of least electrical resistance into the infused tissue of the neighboring bolus.

By placing the injections of electrolytic solution according to the need for thermal tissue damage, a single electrode 14 may deliver heating to a large volume of tissue and the shape of cell necrosis zone 28 created may be placed to create cell necrosis in exactly the area desired. This simplifies the control of cell necrosis zone 28 generation and allows the physician to produce larger lesions in a brief session.

Additionally, the conductivity of the injected electrolytic solution can be decreased. While the advantages of avoiding desiccation adjacent to electrode 14 are maintained, higher ohmic resistance is encountered in the infused tissue. This results in greater heating in the tissue closer to electrode 14. Varying the electrical conductivity of the infused tissue can be used to adjust the size of cell necrosis zone 28 and control the extent of thermal damage.

Disinfectant mediums can also be introduced through electrode 14. Suitable disinfectant mediums include but are not limited to Peridex, an oral rinse containing 0.12% chlorhexidine glucinate (1,1'-hexanethylenebis[5-(p-chlorophenyl)biganide} di-D-gluconate in a base containing water, 11.6% alcohol, glycerin, PEG 40 sorbitan arisoterate, flavor, dosium saccharin, and FD&C Blue No. 1. The disinfectant medium can be introduced prior to, during and after cell necrosis.

Figure 8:
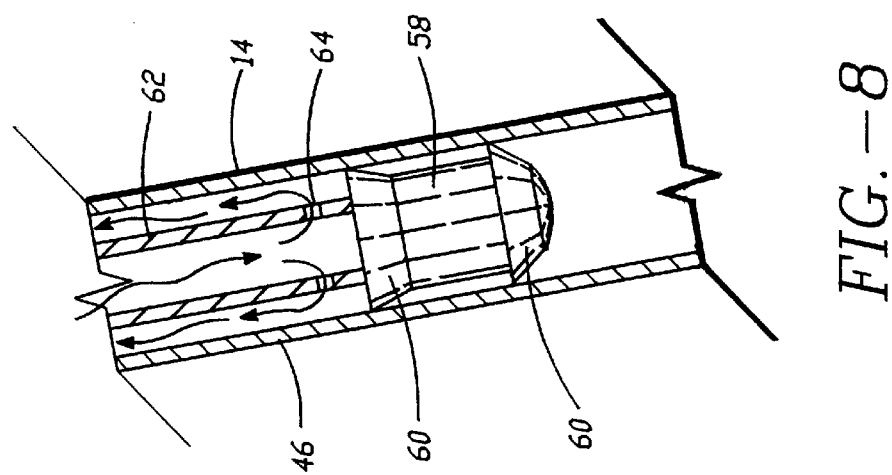
FIG. 8 illustrates a cross-sectional view of the hollow electrode with a sealing plug to control fluid flow.
Figure 7:
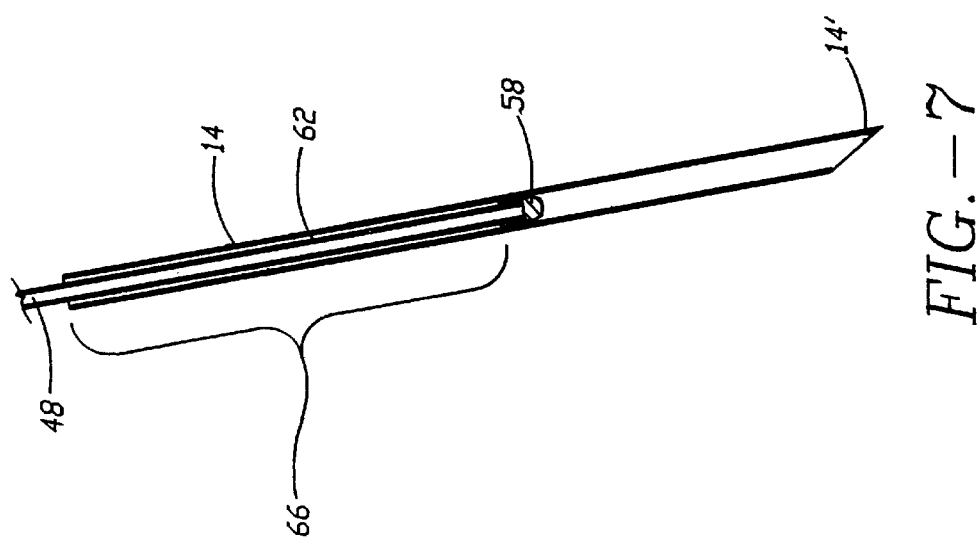
FIG. 7 illustrates a cross-sectional view of the distal end of the electrode of FIG. 6B.

Referring now to FIGS. 6 through 8, electrode 14 may include hollow lumen 48 that is in fluid communication with a control unit 54 which controls the delivery of the fluid via a conduit 56 configured to receive a cooling or heating solution. All of only a portion of a distal portion 14' of electrode 14 is cooled or heating.

The introduction of a cooling fluid reduces cell necrosis of surface layers without the use of insulator 32. This preserves surface mucosal and/or epidermal layers as well as protects a tissue site in the vicinity or in cell necrosis zone 28 from receiving sufficient energy to cause cell necrosis. For instance, it may be desirable to insert electrode 14 into an organ in a position which is adjacent to or even within some feature that must be preserved while treating other areas including but not limited to blood vessels, nerve bundles, glands and the like. The use of cooling permits the delivery of thermal energy in a predetermined pattern while avoiding heating critical structures.

A sealing plug 58 may be positioned in hollow electrode 14 and used to determine the length of electrode 14 that receives the cooling fluid. Sealing plug 58 can include one or more sealing wipers 60 positioned on an outer diameter of sealing plug 50. A fluid tube 62 is coupled to a proximal portion of sealing plug 58 and positioned adjacent to the proximal surface of sealing plug 58. A plurality of fluid distribution ports 64 are formed in fluid tube 62. Cooling fluid, which may be a saline solution or other biologically compatible fluid, is fed from control unit 54 through a small diameter dual lumen tube positioned in conduit 56. Cooling fluid flows through fluid tube 62 to the most distal end where it exits through fluid distribution ports 64 arranged about the outer diameter of fluid tube 62. Cooling fluid then flows within hollow lumen 48 and is in direct contact with the wall structure of electrode 14, which is typically metallic and provides a highly efficient heat transfer. Cooling fluid flows to the proximal end of electrode protected a 14 and through the second lumen of the fluid tube 62, then to control unit 54 which includes both a supply reservoir and a return reservoir to catch and retained the used cooling fluid.

Electrode 14 may have one or more sensors 46 for sensing the temperature of the tissue. This data is fed back to control unit 54 and through an algorithm is stored within a microprocessor memory of control unit 54. Instructions are sent to an electronically controlled micropump (not shown) to deliver fluid through the fluid lines at the appropriate flow rate and duration to provide control of tissue temperature.

The reservoir of control unit 54 may have the ability to control the temperature of the cooling fluid by either cooling the fluid or heating the fluid. Alternatively, a fluid reservoir of sufficient size may be used in which the cooling fluid is introduced at a temperature at or near that of the normal body temperature. Using a thermally insulated reservoir, adequate control of the tissue temperature may be accomplished without need of refrigeration or heating of the cooling fluid.

Cooling zone 66 is adjustable in size and location by moving sealing plug 58 using a stylet 68 which is controlled by a slider 70 position at handpiece 12. In this manner, the position of cooling zone 66 can be moved along the length of electrode 14 and the area which is cooled is then proximal of sealing plug 58. In the event it is desirable to have cooling zone 66 within a length of electrode 14 then a second sealing plug 58 can be positioned at a distance proximal of the first or distal sealing plug 58 and the cooling fluid then re-enters the second lumen of fluid tube 62 at proximal sealing plug 58. The distance between the two sealing plugs 58 determines the length of cooling zone 66. In this example, the distal and proximal sealing plugs 58 move together when activated by stylet 68, re-positioning cooling zone 66.

In another embodiment, the distal and proximal sealing plugs 58 are adjusted individually. This provides the ability to both change the position and length of cooling zone 66.

In typical use, cooling zone 66 is positioned so that a predetermined thickness of mucosal or epidermal tissue 72 on the surface of the tissue to be treated 74 is protected as indicated at 75 while the desired cell necrosis zone 28 is formed.

An alternative feature is the ability to indicate to the physician the amount of electrode 14 length that is inserted into the tissue and the depth of protected area 32. To accomplish this, a portion of cell necrosis apparatus 10 comes in contact with mucosal or epidermal surface 72. This can be achieved with a contact collar 76 or with a larger surface that is contoured to fit against the organ or anatomical feature to be treated. The dimensional relationship between contact collar 76 and handpiece 12 is maintained by a sleeve 78 through which electrode 14, fluid tube 62 and stylet 68 all pass. With this dimensional relationship maintained, it is then possible to indicate with indexing pointers on handpiece 12 the distance of electrode 14 distal of contact collar 76 or the surface of cell necrosis apparatus 10. The distance of cooling zone 66 is then positioned distal of contact collar 76 or the surface cell necrosis apparatus 10. Because all cooling is within electrode 14 and external insulator 32 is not used, electrode 14 penetrates easily through the tissue without drag or resistance that is present when insulator 32 is present.

In another embodiment, sealing plugs 58 and direct flow of cooling fluid are replaced with a slidable inner cooling plug which may be constructed of a material with efficient heat transfer characteristics. Suitable cooling plug materials include but are not limited to copper, beryllium copper, silver and aluminum alloys. Cooling plug is sized to fit intimately against the inner surface of needle 14. This allows transfer of heat from electrode 14 to cooling the plug. In this embodiment, cooling plug has interior passageways through which cooling fluid passes. This draws heat from the cooling plug.

Although this embodiment does not provide the highly efficient cooling available by having the cooling fluid in direct contact with the inner surface of electrode 14, a more thorough isolation of the cooling fluid from the body is provided. This results from reducing the possibility of experiencing some leakage past sealing plug 58 of the other embodiment.

In yet another embodiment of cooling, heat pipe technology is used. A sealed compartment contains a mixture of gases which have the ability to rapidly vaporize and condense at temperatures which facilitate the transfer of heat with high efficiency. In this embodiment, a cooling module within handpiece 12 cools the proximal end of the tubular heat pipe and heat is conducted from cooling zone 66 to the cooling module.

Cell necrosis apparatus 10 can be used to create cell necrosis in other structures that affect airway passages including but not limited to the uvula, turbinate structures, soft palate structures and tonsils.

Figure 9:
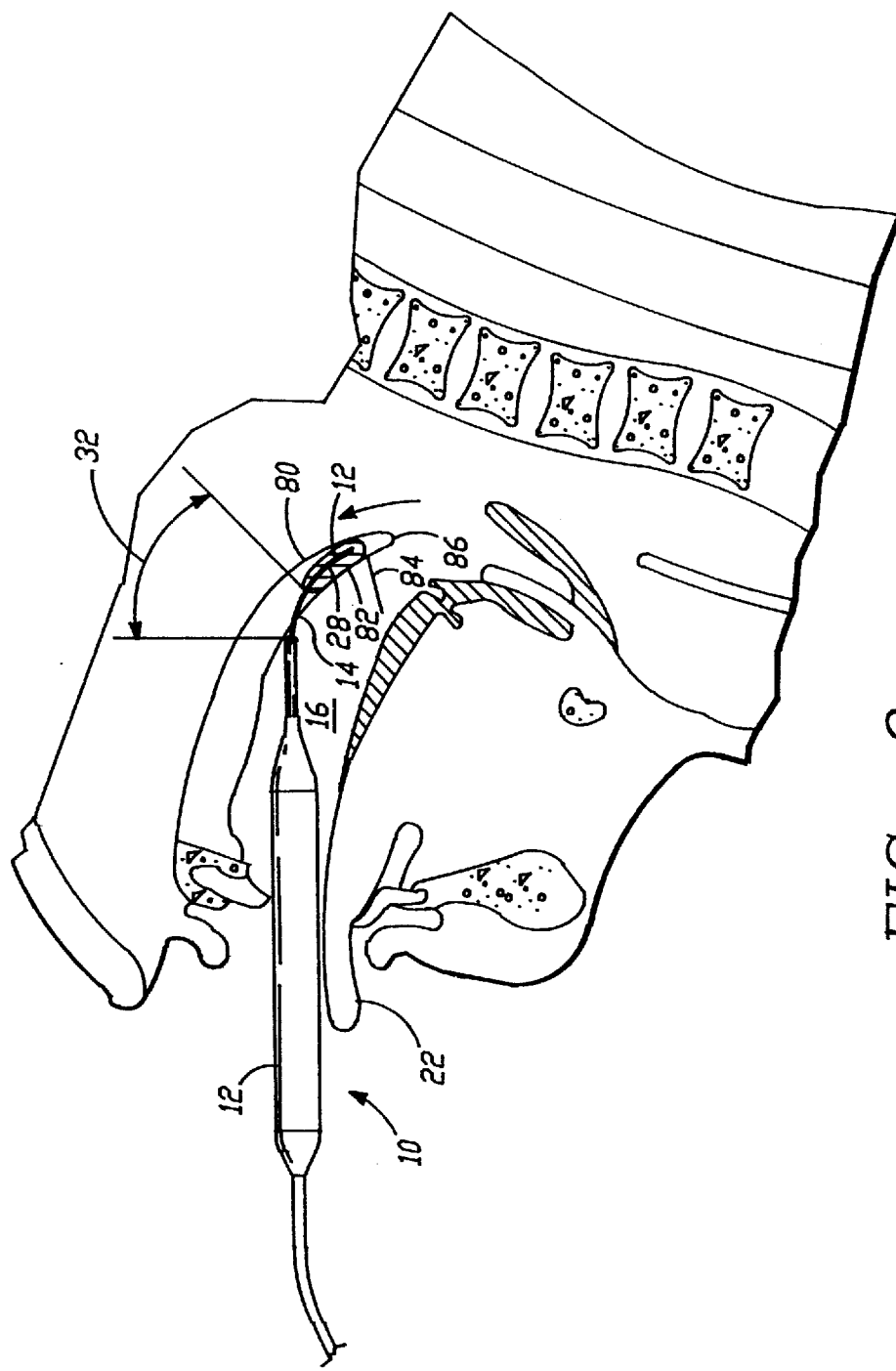
FIG. 9 illustrates the creation of cell necrosis zones in the uvula and the repositioning of the uvula in the oral cavity.
Figure 10:
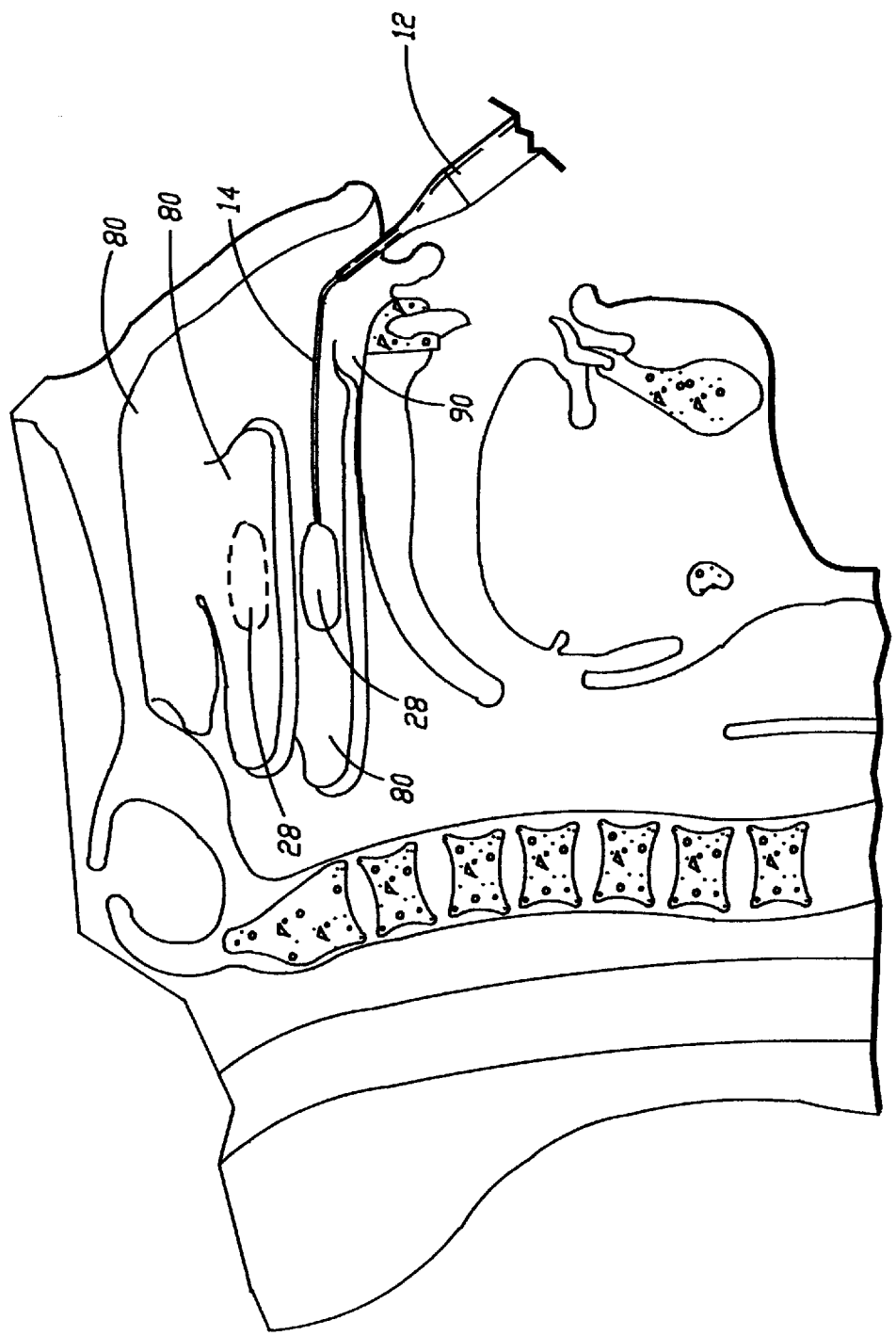
FIG. 10 illustrates the creation of cell necrosis zones in the turbinates and the repositioning of the turbinates in the nasal cavity.

As shown in FIGS. 9 and 10, cell necrosis apparatus 10 is used to create one or more cell necrosis zones 28 in uvula 80. Electrode 12 is configured to be maneuverable in oral cavity 16, pierce an uvula exterior surface, advance into an interior of the uvula a sufficient distance to a tissue site, deliver electromagnetic energy to the tissue site and create controlled cell necrosis. The creation of cell necrosis zones 28 repositions the treated uvula 80 in oral cavity 16 (as indicated by the arrows) while substantially preserving an uvula mucosal layer 82 at an exterior of uvula 80. Cell necrosis zones 28 are created in uvula 80 without creating an ulceration line at a tip 86 of uvula 80. Controlled cell necrosis tightens and reshapes uvula 80.

In creating uvula 80, electrode 12 can have a variety of geometric configurations and may include a curved distal end. The different cell necrosis zones 28 can be stacked in one or more treatment sessions. This permits the physician to control the amount of tissue treated and to assess the results of each session before proceeding with additional procedures. Because exterior mucosal tissue is spared, the patient experiences little pain or discomfort.

Referring now to FIG. 10, cell necrosis apparatus 10 is used to create cell necrosis zones 28 in a turbinate structure 88, which can include the interior nasal concha, the middle nasal concha, the superior nasal concha, and combinations thereof. Electrode 14 is configured to be maneuverable in a nostril, pierce a turbinate structure surface 90 advance into an interior of turbinate structure 88 a sufficient distance to a tissue site, deliver electromagnetic energy to the tissue site and create controlled cell necrosis of turbinate structure 88 to increase a size of a nasal passageway 90.

Figure 11:
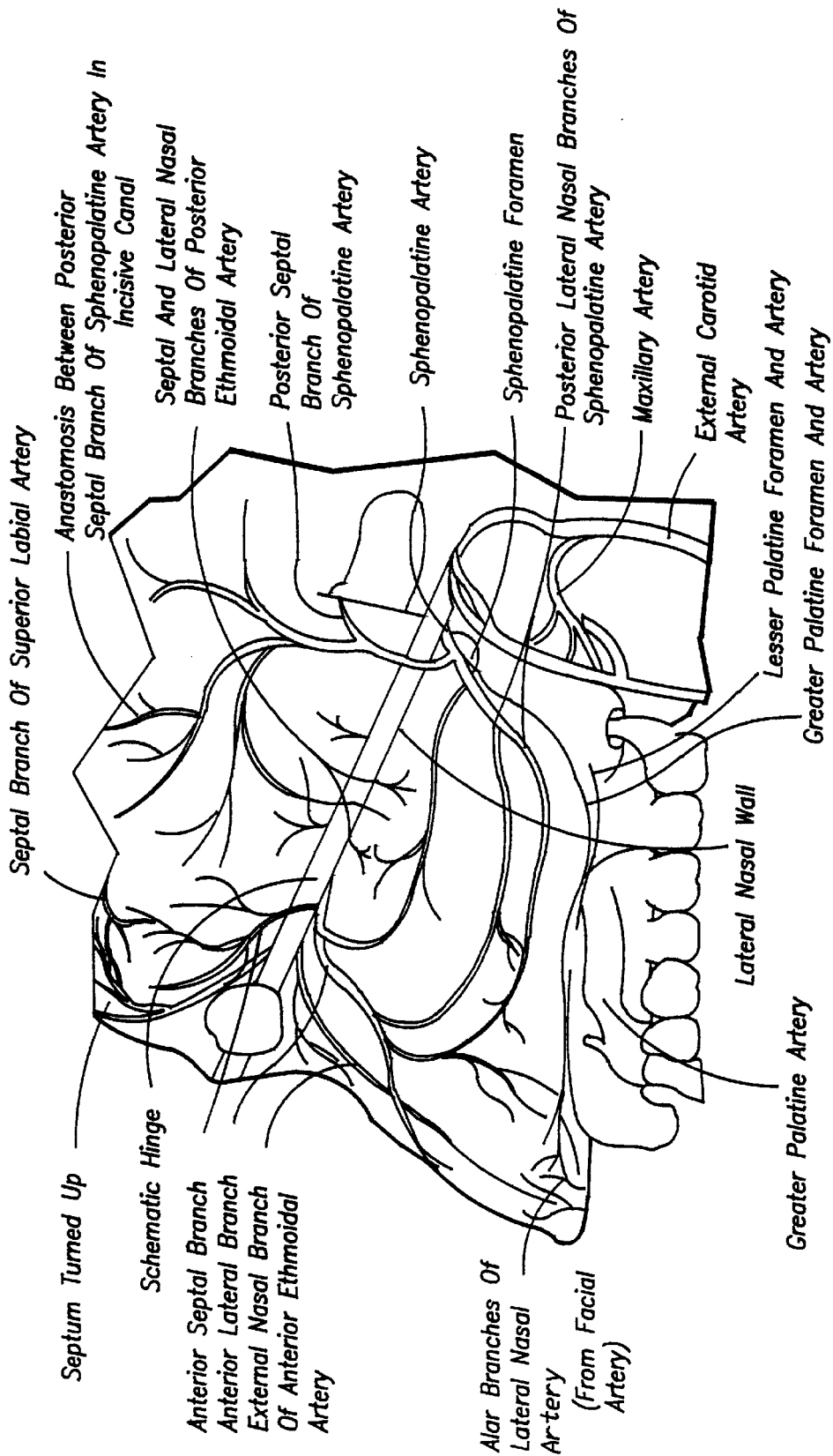
FIG. 11 illustrates a cross-sectional view of the arteries of the nasal cavity.
Figure 12:
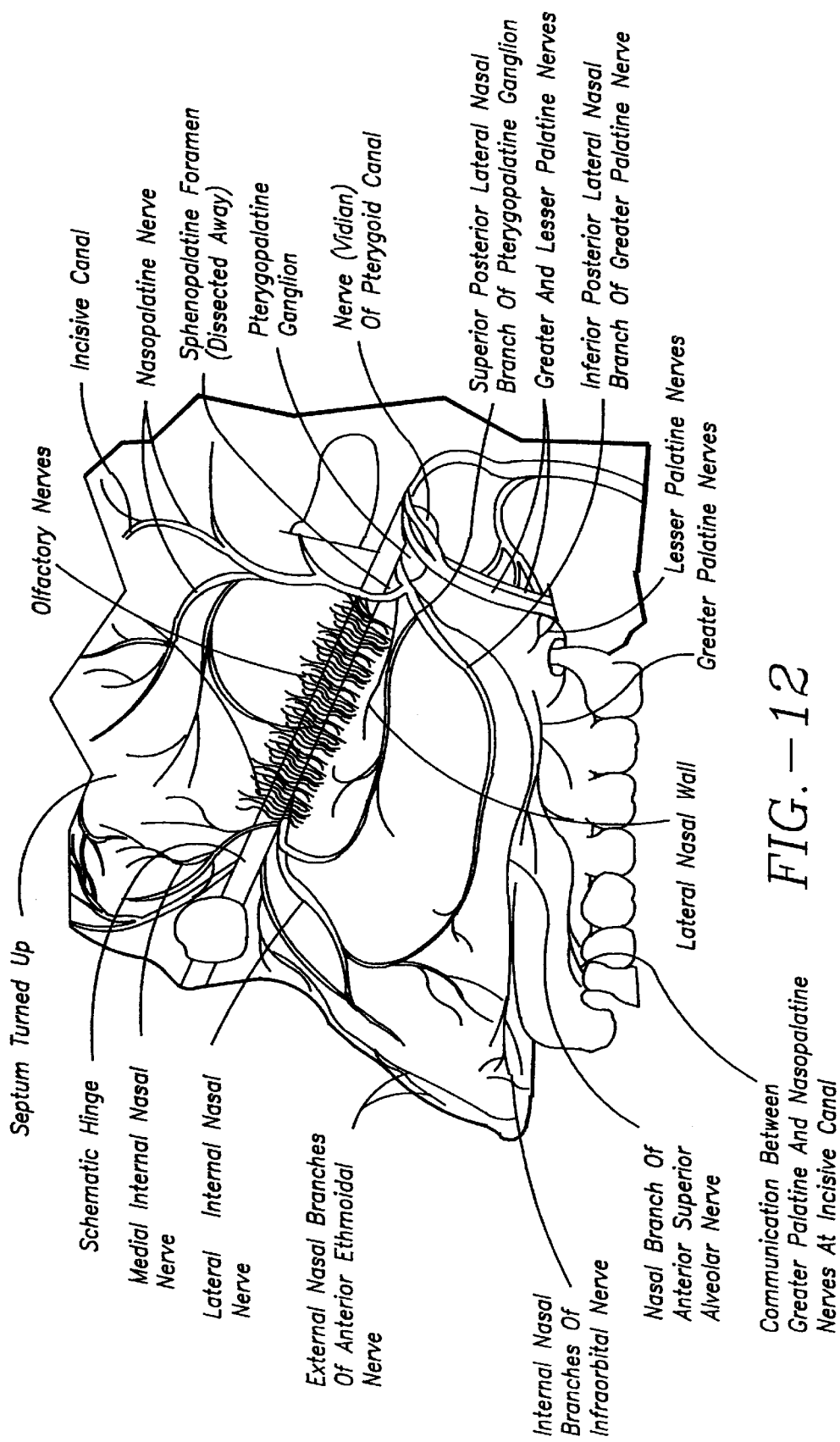
FIG. 12 depicts a cross-sectional view of the head illustrating the arteries of the nasal cavity.

Sufficient electromagnetic energy is delivered to the tissue site to create controlled cell necrosis of the turbinate structure without sufficiently limiting blood flow to the optic nerve and/or the retina (FIG. 11). As shown in FIG. 12 disruption of the blood flow to the optic nerve and/or retina can sufficiently damage the optic nerve and/or retina and create a permanent impairment of vision.

Referring again to FIG. 10, electrode 14 creates cell necrosis zones 28 to reduce the size turbinate structure 88 by removing only so much of turbinate structure 88 to increase the size of the nasal passageway but insufficient to create a permanent, (i) dysosmic state, (ii) dry nose condition, (iii) atrophic rhinitis state, (iv) a loss of ciliary function or (v) damage to the nerves of nasal cavity creating a permanent loss of nasal and facial structure activity. The creation of the ablation zones in turbinate structure 88 repositions turbinate structure 88. In one embodiment, no more than 33% of the mucosal layer of the lower turbinate is removed. Further removal may create the dysosmic state, a permanent dry nose condition and/or a loss of ciliary function.

Figure 13:
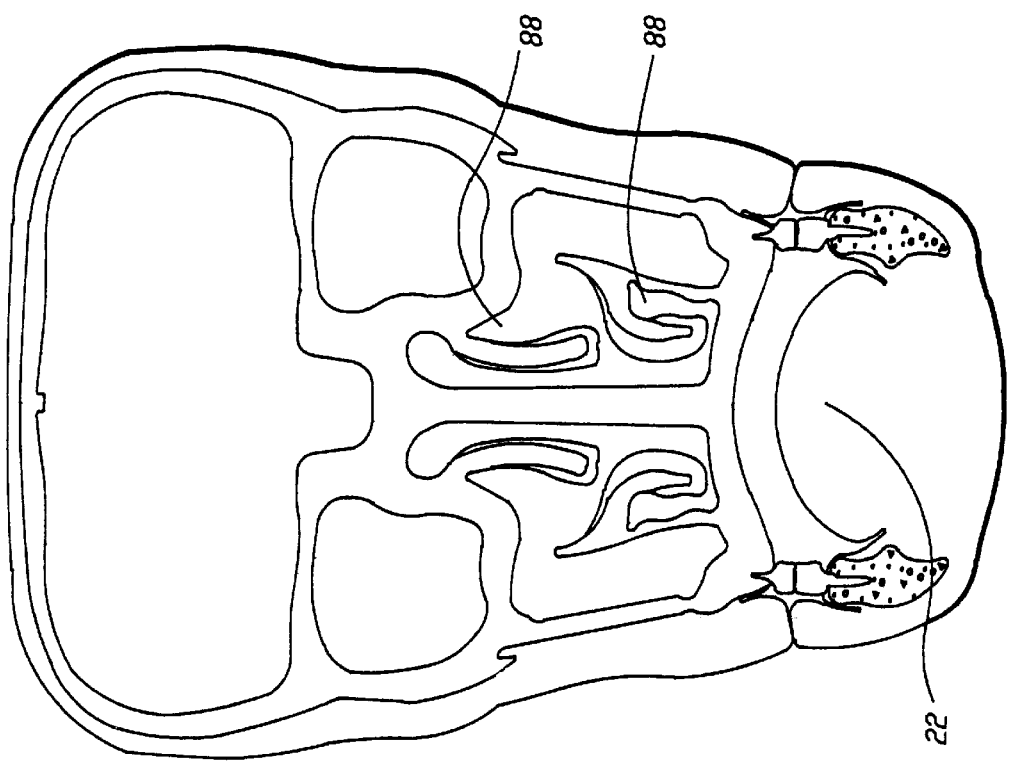
FIG. 13 depicts a cross-sectional view of the head taken laterally through the nasal cavity illustrating a shrinkage of the turbinates following treatment with the cell necrosis apparatus of the present invention.
Figure 14:
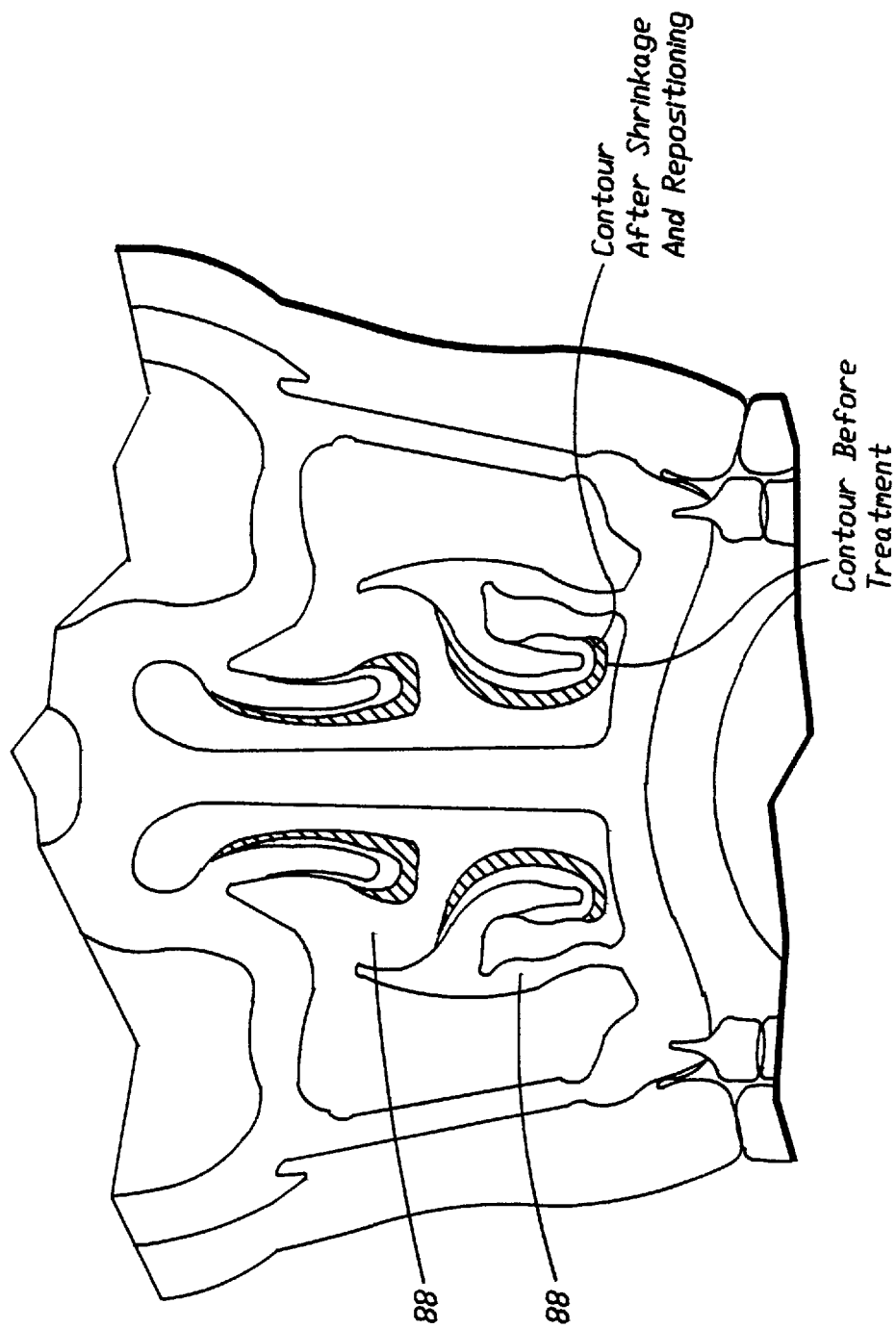
FIG. 14 depicts a close up cross-sectional view of FIG. 13.

As illustrated in FIGS. 13 and 14, cell necrosis apparatus 10 provides controlled ablation of turbinate structures 88 and the resulting turbinate structure is repositioned in the nasal cavity, and can "open up" the nasal cavity for allergy sufferers and the like.

In another embodiment (FIGS. 15 and 16), cell necrosis apparatus 10 reduces a volume of a selected site in an interior of a soft palate structure 94. Electrode 14 is configured to be maneuverable in oral cavity 16, pierce a soft palate structure surface 96, advance a sufficient distance to a tissue site, deliver electromagnetic energy to the tissue site, create controlled cell necrosis zones 28 and reposition soft palate structure 94 in oral cavity 16 with reduced necrosis of an exterior mucosal surface 98 of soft palate structure 94. The creation of cell necrosis zones 28 repositions soft palate structure 94 and tightens the interior tissue of soft palate structure as illustrated by the arrows.

Again, various imaging devices and methods, well known in the art, may be used to position electrode 14 and/or determine the amount of cell necrosis.

Figure 17:
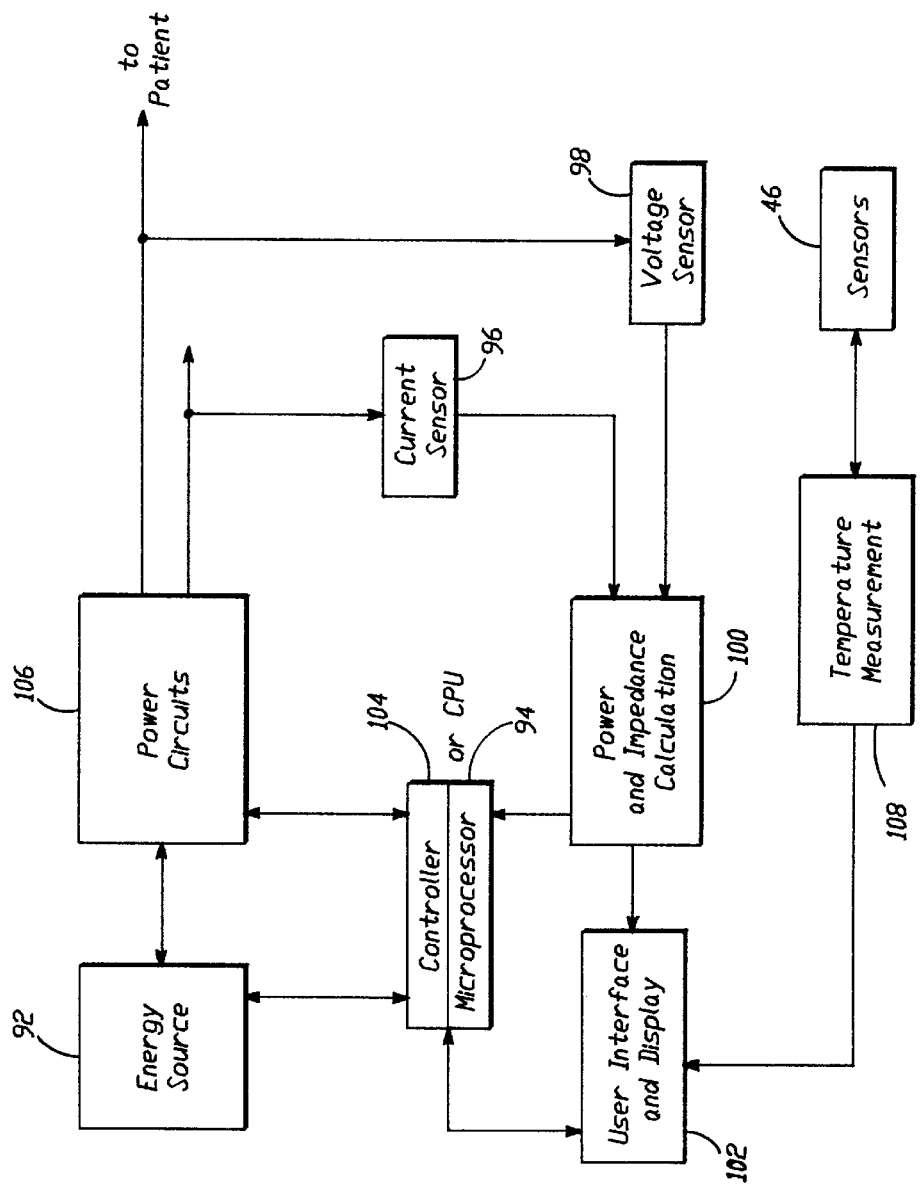
FIG. 17 depicts a block diagram of the feed back control system that can be used with the cell necrosis apparatus as shown in FIGS. 1A–C.

In one embodiment, cell necrosis apparatus 10 is coupled to an open or closed loop feedback system. Referring now to FIG. 17 an open or closed loop feedback system couples sensor 46 to energy source 92. In this embodiment, electrode 14 is one or more RF electrodes 14. It will be appreciated that other energy delivery devices 14 can also be used with the feedback system.

The temperature of the tissue, or of RF electrode 14 is monitored, and the output power of energy source 92 adjusted accordingly. Additionally, the level of disinfection in the oral cavity can be monitored. The physician can, if desired, override the closed or open loop system. A microprocessor can be included and incorporated in the closed or open loop system to switch power on and off, as well as modulate the power. The closed loop system utilizes a microprocessor 94 to serve as a controller, monitor the temperature, adjust the RF power, analyze at the result, refeed the result, and then modulate the power.

With the use of sensor 46 and the feedback control system a tissue adjacent to RF electrode 14 can be maintained at a desired temperature for a selected period of time without impeding out. Each RF electrode 14 is connected to resources which generate an independent output. The output maintains a selected energy at RF electrode 14 for a selected length of time.

Current delivered through RF electrode 14 is measured by current sensor 96. Voltage is measured by voltage sensor 98. Impedance and power are then calculated at power and impedance calculation device 100. These values can then be displayed at user interface and display 102. Signals representative of power and impedance values are received by a controller 104.

A control signal is generated by controller 104 that is proportional to the difference between an actual measured value, and a desired value. The control signal is used by power circuits 106 to adjust the power output in an appropriate amount in order to maintain the desired power delivered at respective RF electrodes 14.

In a similar manner, temperatures detected at sensor 46 provide feedback for maintaining a selected power. Temperature at sensor 46 are used as safety devices to interrupt the delivery of energy when maximum pre-set temperatures are exceeded. The actual temperatures are measured at temperature measurement device 102, and the temperatures are displayed at user interface and display 102. A control signal is generated by controller 104 that is proportional to the difference between an actual measured temperature and a desired temperature. The control signal is used by power circuits 106 to adjust the power output in an appropriate amount in order to maintain the desired temperature delivered at the sensor 46. A multiplexer can be included to measure current, voltage and temperature, at the sensor 46, and energy can be delivered to RF electrode 14 in monopolar or bipolar fashion.

Controller 104 can be a digital or analog controller, or a computer with software. When controller 104 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 102 includes operator controls and a display. Controller 104 can be coupled to imaging systems, including but not limited to ultrasound, CT scanners, X-ray, MRI, mammographic X-ray and the like. Further, direct visualization and tactile imaging can be utilized.

The output of current sensor 96 and voltage sensor 98 is used by controller 104 to maintain a selected power level at RF electrode 14. The amount of RF energy delivered controls the amount of power. A profile of power delivered can be incorporated in controller 104 and a preset amount of energy to be delivered may also be profiled.

Circuitry, software and feedback to controller 104 result in process control, and the maintenance of the selected power setting that is independent of changes in voltage or current, and used to change, (i) the selected power setting, (ii) the duty cycle (on-off time), (iii) bipolar or monopolar energy delivery and (iv) fluid delivery, including flow rate and pressure. These process variables are controlled and varied, while maintaining the desired delivery of power independent of changes in voltage or current, based on temperatures monitored at sensor 46.

Figure 18:
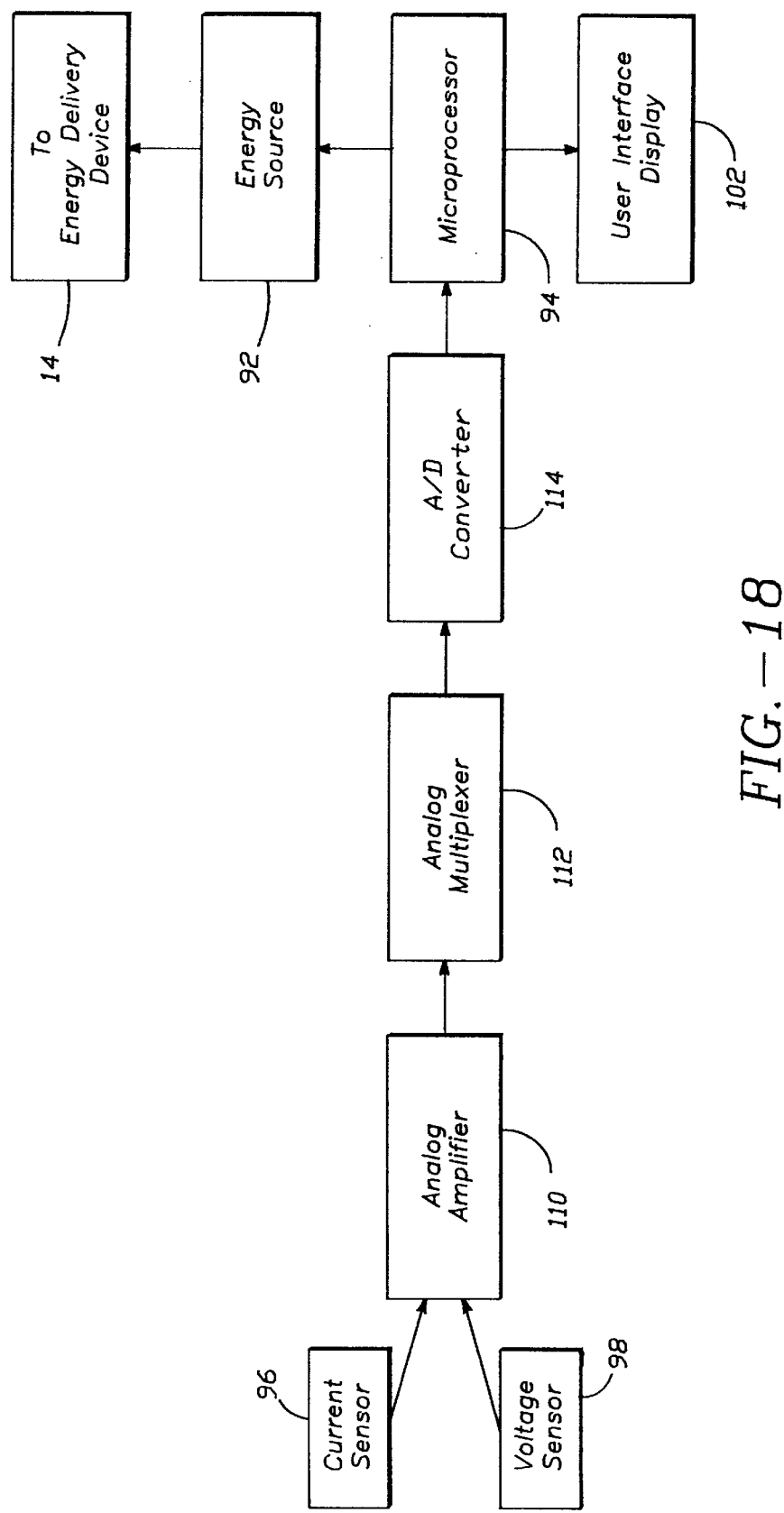
FIG. 18 depicts a block diagram of an analog amplifier, analog multiplexer and microprocessor used with the feedback control system of FIG. 17.

Referring to FIG. 18, current sensor 96 and voltage sensor 98 are connected to the input of an analog amplifier 110. Analog amplifier 110 can be a conventional differential amplifier circuit for use with sensor 46. The output of analog amplifier 110 is sequentially connected by an analog multiplexer 106 to the input of A/D converter 108. The output of analog amplifier 110 is a voltage which represents the respective sensed temperatures. Digitized amplifier output voltages are supplied by A/D converter 108 to microprocessor 94. Microprocessor 94 may be a type 68HCII available from Motorola. However, it will be appreciated that any suitable microprocessor or general purpose digital or analog computer can be used to calculate impedance or temperature.

Microprocessor 94 sequentially receives and stores digital representations of impedance and temperature. Each digital value received by microprocessor 94 corresponds to different temperatures and impedances.

Calculated power and impedance values can be indicated on user interface and display 102. Alternatively, or in addition to the numerical indication of power or impedance, calculated impedance and power values can be compared by microprocessor 94 with power and impedance limits. When the values exceed predetermined power or impedance values, a warning can be given on user interface and display 102, and additionally, the delivery of RF energy can be reduced, modified or interrupted. A control signal from microprocessor 94 can modify the power level supplied by energy source 92.

Figure 19:
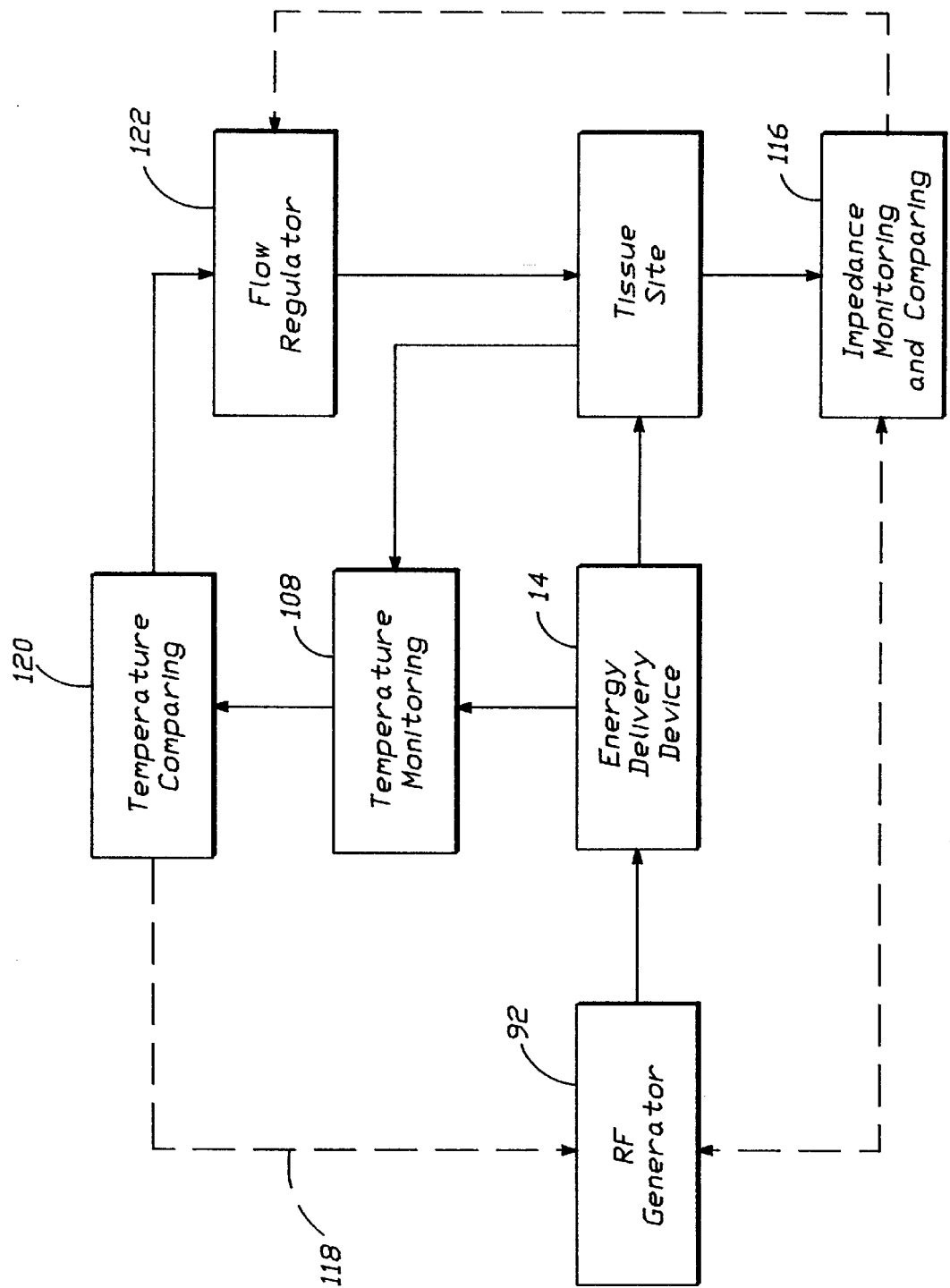
FIG. 19 depicts a block diagram of a current sensor and voltage sensor connected to the analog amplifier of FIG. 18.

FIG. 19 illustrates a block diagram of a temperature/impedance feedback system that can be used to control temperature control fluid flow rate through introducer 14. Energy is delivered to RF electrode 14 by energy source 92, and applied to tissue. A monitor 116 ascertains tissue impedance, based on the energy delivered to tissue, and compares the measured impedance value to a set value. If the measured impedance exceeds the set value a disabling signal 112 is transmitted to energy source 92, ceasing further delivery of energy to electrode 14. If measured impedance is within acceptable limits, energy continues to be applied to the tissue. During the application of energy sensor 46 measures the temperature of tissue and/or electrode 14. A comparator 120 receives a signal representative of the measured temperature and compares this value to a preset signal representative of the desired temperature. Comparator 120 sends a signal to a flow regulator 122 representing a need for a higher temperature control fluid flow rate, if the tissue temperature is too high, or to maintain the flow rate if the temperature has not exceeded the desired temperature.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A cell necrosis apparatus to reduce a volume of a selected site in an interior of a tongue in an oral cavity, comprising:
   a handpiece means;
   an electrode means coupled to a distal portion of the handpiece means including a tissue piercing distal end, the electrode means being configured to be maneuverable in the oral cavity to pierce a tongue surface and advance into an interior of the tongue a sufficient distance to a tissue site, deliver electromagnetic energy to the tissue site and create controlled cell necrosis without damaging a main branch of the hypoglossal nerve; and
   a cable means coupled to the electrode means.

2. The apparatus of claim 1, wherein the electrode means is an RF electrode means.

3. The apparatus of claim 2, further comprising:
   an RF energy source coupled to the RF electrode means.

4. The apparatus of claim 1, further comprising:
   a cooling device means coupled to the electrode means.

5. The apparatus of claim 4, further comprising:
   a flow rate control device means coupled to the cooling device means and configured to control a cooling medium flow rate through the cooling device means.

6. The apparatus of claim 1, further comprising:
an insulator means at least partially positioned around an exterior of the electrode means.

7. The apparatus of claim 6, further comprising:
a sensor means coupled to the electrode means.

8. The apparatus of claim 1, further comprising:
a sensor means positioned at a distal end of the electrode means.

9. The apparatus of claim 1, further comprising:
a feedback control device means coupled to the electrode means, a sensor means and an RF energy source means.

10. The apparatus of claim 1, further comprising:
an infusion medium source means coupled to the electrode means.

11. The apparatus of claim 1, where in the electrode means has an electrode means advancement length extending from an exterior of the handpiece means to the interior of the tongue, wherein the advancement length is sufficient to position the energy delivery surface at the selected site and deliver sufficient electromagnetic energy to create cell necrosis without damaging a main branch of a hypoglossal nerve.

12. A cell necrosis apparatus to reduce a volume of a selected site in an interior of a uvula, comprising:
a handpiece means;
an electrode means coupled to a distal portion of the handpiece means including a tissue piercing distal end, the electrode means being configured to be maneuverable in the oral cavity to pierce a uvula surface and advance into an interior of the uvula a sufficient distance to a tissue site, deliver electromagnetic energy to the tissue site and create controlled cell necrosis and a repositioning of the uvula in the oral cavity while substantially preserving an uvula mucosal layer at an exterior of the uvula; and
a cable means coupled to the electrode means.

13. The apparatus of claim 12, wherein the electrode means is configured to create controlled cell necrosis and the repositioning of the uvula without creating an ulceration line at a tip of the uvula.

14. The apparatus of claim 12, wherein the electrode means is configured to create controlled cell necrosis and a tightening of a uvula tissue to reposition the uvula.

15. The apparatus of claim 12, wherein the electrode means is configured to create controlled cell necrosis and a reshaping of a uvula tissue to reposition the uvula.

16. The apparatus of claim 12, wherein the electrode means is an RF electrode means.

17. The apparatus of claim 13, further comprising:
an RF energy source means coupled to the RF electrode means.

18. The apparatus of claim 12, further comprising:
a cooling device means coupled to the electrode means.

19. The apparatus of claim 18, further comprising:
a flow rate control device means coupled to the cooling device means and configured to control a cooling medium flow rate through the cooling device means.

20. The apparatus of claim 12, further comprising:
an insulator means at least partially positioned around an exterior of the electrode means.

21. The apparatus of claim 12, further comprising:
a sensor means coupled to the electrode means.

22. The apparatus of claim 12, further comprising:
a sensor means positioned at a distal end of the electrode means.

23. The apparatus of claim 12, further comprising:
a feedback control device means coupled to the electrode means, a sensor means and an RF energy source means.

24. The apparatus of claim 12, further comprising:
an infusion medium source means coupled to the electrode means.

25. The apparatus of claim 12, wherein the electrode means has an electrode means advancement length extending from an exterior of the handpiece means to the interior of the uvula, wherein the advancement length is sufficient to position the energy delivery surface at the selected site and deliver sufficient electromagnetic energy to create cell necrosis with reduced necrosis of an exterior mucosal surface.

26. A cell necrosis apparatus to reduce a volume of a selected site in an interior of a turbinate structure, comprising:
a handpiece means;
an electrode means coupled to a distal portion of the handpiece means including a tissue piercing distal end, the electrode means being configured to be maneuverable in a nostril to pierce a turbinate structure exterior surface, advance a sufficient distance in an interior of the turbinate structure to a tissue site, deliver electromagnetic energy to the tissue site and create controlled cell necrosis of the turbinate structure to increase a size of a nasal passageway without sufficiently limiting blood flow to the optic nerve and create a permanent impairment of vision; and
a cable means coupled to the electrode means.

27. The apparatus of claim 26, wherein the electrode means creates controlled cell necrosis without creating a permanent dysosmic state.

28. The apparatus of claim 26, wherein the electrode means creates controlled cell necrosis of the mucosal layer without creating a permanent dry nose condition.

29. The apparatus of claim 26, wherein the electrode means creates controlled cell necrosis of the mucosal layer without creating a permanent atrophic rhinitis condition.

30. The apparatus of claim 26, wherein the electrodes means creates controlled cell necrosis of the mucosal layer without creating a permanent loss of ciliary function.

31. The apparatus of claim 26, wherein the electrode means is an RF electrode means.

32. The apparatus of claim 30, further comprising:
an RF energy source means coupled to the RF electrode means.

33. The apparatus of claim 26, further comprising:
a cooling device means coupled to the electrode means.

34. The apparatus of claim 26, further comprising:
a flow rate control device means coupled to the cooling device means and configured to control a cooling medium flow rate through the cooling device means.

35. The apparatus of claim 26, further comprising:
an insulator means at least partially positioned around an exterior of the electrode means.

36. The apparatus of claim 26, further comprising:
a sensor means coupled to the electrode means.

37. The apparatus of claim 26, further comprising:
a sensor means positioned at a distal end of the electrode means.

38. The apparatus of claim 26, further comprising:
a feedback control device means coupled to the electrode means, a sensor means and an RF energy source means.

39. The apparatus of claim 26, further comprising:
an infusion medium source means coupled to the electrode means.

40. The apparatus of claim 26, wherein the electrode means has an electrode means advancement length extending from an exterior of the handpiece means to the interior of the turbinate structure, wherein the advancement length is sufficient to position the energy delivery surface at the selected site and deliver sufficient electromagnetic energy to the selected tissue site and create controlled cell necrosis of a mucosal layer of a turbinate bone while preserving a sufficient amount of turbinate bone and prevent creating a permanent dry nose condition.

41. A cell necrosis apparatus to reduce a volume of a selected site in an interior of a soft palate structure, comprising:
a handpiece means;
an electrode means coupled to a distal portion of the handpiece means including a tissue piercing distal end, the electrode means being configured to be maneuverable in an oral cavity to pierce a soft palate structure surface and advance into an interior of the soft palate structure a sufficient distance to a tissue site, deliver electromagnetic energy to the tissue site, create controlled cell necrosis and reposition the soft palate structure in an oral cavity with reduced necrosis of an exterior mucosal surface of the soft palate structure; and
a cable means coupled to the electrode means.

42. The apparatus of claim 41, wherein the electrode means is configured to create controlled cell necrosis and a tightening of a soft palate tissue to reposition the soft palate structure.

43. The apparatus of claim 41, wherein the electrode means is configured to create controlled cell necrosis and a reshaping of a soft palate tissue to reposition the soft palate structure.

44. The apparatus of claim 41, wherein the electrode means is an RF electrode means.

45. The apparatus of claim 44, further comprising:
an RF energy source means coupled to the RF electrode means.

46. The apparatus of claim 41, further comprising:
a cooling device means coupled to the electrode means.

47. The apparatus of claim 46, further comprising:
a flow rate control device means coupled to the cooling device means and configured to control a cooling medium flow rate through the cooling device means.

48. The apparatus of claim 41, further comprising:
an insulator means at least partially positioned around an exterior of the electrode means.

49. The apparatus of claim 41, further comprising:
a sensor means coupled to the electrode means.

50. The apparatus of claim 41, further comprising:
a sensor means positioned at a distal end of the electrode means.

51. The apparatus of claim 41, further comprising:
a feedback control device means coupled to the electrode means, a sensor means and an RF energy source means.

52. The apparatus of claim 41, further comprising:
an infusion medium source means coupled to the electrode means.

53. The apparatus of claim 41, wherein the electrode means has an electrode means advancement length extending from an exterior of the handpiece means to the interior of the soft palate structure, wherein the advancement length is sufficient to position the energy delivery surface at the selected site and deliver sufficient electromagnetic energy to create cell necrosis with reduced necrosis of an exterior mucosal surface of the soft palate structure.

54. A cell necrosis apparatus to reduce a volume of a selected site in an interior of a turbinate structure, comprising:
a handpiece means;
an electrode means coupled to a distal portion of the handpiece means including a tissue piercing distal end, the electrode means being configured to be maneuverable in a nostril to pierce a turbinate structure exterior surface, advance a sufficient distance in an interior of the turbinate structure to a tissue site, deliver electromagnetic energy to the tissue site and create controlled cell necrosis of the turbinate structure to increase a size of a nasal passageway without sufficiently limiting blood flow to the retina and create a permanent impairment of vision; and
a cable means coupled to the electrode means.

55. The apparatus of claim 54, wherein the electrode means creates controlled cell necrosis without creating a permanent dysosmic state.

56. The apparatus of claim 54, wherein the electrode means creates controlled cell necrosis of the mucosal layer without creating a permanent dry nose condition.

57. The apparatus of claim 54, wherein the electrode means creates controlled cell necrosis of the mucosal layer without creating a permanent atrophic rhinitis condition.

58. The apparatus of claim 54, wherein the electrodes means creates controlled cell necrosis of the mucosal layer without creating a permanent loss of ciliary function.

59. The apparatus of claim 54, wherein the electrode means is an RF electrode means.

60. The apparatus of claim 59, further comprising:
an RF energy source means coupled to the RF electrode means.

61. The apparatus of claim 54, further comprising:
a cooling device means coupled to the electrode means.

62. The apparatus of claim 54, further comprising:
an insulator means at least partially positioned around an exterior of the electrode means.

63. The apparatus of claim 54, further comprising:
a sensor means coupled to the electrode means.

64. A method of ablating a portion of a uvula, comprising steps of:
providing an RF ablation apparatus including a handle, an RF ablation electrode coupled to the handle, the RF ablation electrode having a distal end sharpened sufficiently to pierce the uvula, and an RF energy source coupled to the ablation electrode;
introducing at least a portion of the RF ablation apparatus including the ablation electrode including the ablation electrode distal end into a mouth cavity;
positioning the RF ablation apparatus distal end adjacent to the uvula;
urging the RF ablation electrode distal end against the uvula to pierce and extend within the uvula;
applying RF ablation energy to the ablation electrode; and
removing the RF ablation electrode distal end from the uvula.

65. The method of claim 64, the step of providing an RF ablation apparatus further comprising a step of providing an RF ablation apparatus wherein the distal end of the RF ablation electrode is sufficiently sharpened to pierce the uvula while it is unsupported to remain in a stationary position.

66. The method of claim 64, the step of providing an RF ablation apparatus further comprising a step of providing an RF ablation apparatus wherein the RF ablation electrode is a needle electrode.

67. The method of claim 64, the step of providing an RF ablation apparatus further comprising a step of providing an RF ablation apparatus including a second ablation electrode with a distal end sharpened sufficiently to pierce the uvula.

68. The method of claim 67, further comprising steps of urging the second ablation electrode distal end against the uvula to pierce and extend within the uvula; and applying RF ablation energy to the second ablation electrode.

69. The method of claim 68, the step of providing an RF ablation apparatus further comprising a step of providing an RF ablation apparatus that the RF ablation apparatus operates in a bipolar mode.

70. The method of claim 64, the step of providing an RF ablation apparatus further comprising a step of providing an RF ablation apparatus that the RF ablation apparatus operates in a monopolar mode.

71. The method of claim 70, the step of providing an RF ablation apparatus further comprising a step of providing an RF ablation apparatus that includes a ground pad electrode coupled to the RF energy source.

72. The method of claim 64, the step of providing an RF ablation apparatus further comprising a step of providing an RF ablation apparatus that includes an advancement and retraction device interposed between the handle and the RF ablation electrode, the step of urging the RF ablation apparatus distal end against the uvula further comprising a step of actuating the advancement and retraction device to advance the RF ablation electrode distal end within the uvula a desired distance.

73. The method of claim 72, the step of removing the RF ablation electrode distal end from the uvula further comprising a step of actuating the advancement and retraction device to retract the RF ablation electrode distal end from within the uvula.

74. A method of ablating a portion of a soft palate, comprising steps of:
   providing an RF ablation apparatus including a handle, an RF ablation electrode coupled to the handle, the RF ablation electrode having a distal end sharpened sufficiently to pierce the soft palate, and an RF energy source coupled to the ablation electrode;
   introducing at least a portion of the RF ablation apparatus including the ablation electrode distal end into a mouth cavity;
   positioning the RF ablation apparatus distal end adjacent to the soft palate;
   urging the RF ablation electrode distal end against the soft palate to pierce and extend within the soft palate;
   applying RF ablation energy to the ablation electrode; and
   removing the RF ablation electrode distal end from the soft palate.

75. The method of claim 74, the step of providing an RF ablation apparatus further comprising a step of providing an RF ablation apparatus wherein the distal end of the RF ablation electrode is sufficiently sharpened to pierce the soft palate while it is unsupported to remain in a stationary position.

76. The method of claim 74, the step of providing an RF ablation apparatus further comprising a step of providing an RF ablation apparatus wherein the RF ablation electrode is a needle electrode.

77. The method of claim 74, the step of providing an RF ablation apparatus further comprising a step of providing an RF ablation apparatus including a second ablation electrode with a distal end sharpened sufficiently to pierce the soft palate.

78. The method of claim 77 further comprising steps of urging the second ablation electrode distal end against the soft palate to pierce and extend within the soft palate; and
   applying RF ablation energy to the second ablation electrode.

79. The method of claim 78, the step of providing an RF ablation apparatus further comprising a step of providing an RF ablation apparatus that the RF ablation apparatus operates in a bipolar mode.

80. The method of claim 74, the step of providing an RF ablation apparatus further comprising a step of providing an RF ablation apparatus that the RF ablation apparatus operates in a monopolar mode.

81. The method of claim 80, the step of providing an RF ablation apparatus further comprising a step of providing an RF ablation apparatus that includes a ground pad electrode coupled to the RF energy source.

82. The method of claim 74, the step of providing an RF ablation apparatus further comprising a step of providing an RF ablation apparatus that comprises an advancement and retraction device interposed between the handle and the RF ablation electrode, the step of urging the RF ablation apparatus distal end against the soft palate further comprising a step of actuating the advancement and retraction device to advance the RF ablation electrode distal end within the soft palate a desired distance.

83. The method of claim 82, the step of removing the RF ablation electrode distal end from the soft palate further comprising a step of actuating the advancement and retraction device to retract the RF ablation electrode distal end from within the soft palate.

* * * * *